(12) United States Patent
Lambert et al.

(10) Patent No.: US 10,082,807 B2
(45) Date of Patent: Sep. 25, 2018

(54) METHOD OF PREPARING A CERTIFIED TARGET PRODUCT FROM A MIXTURE OF COMPONENTS BY SPECTRAL ANALYSIS

(71) Applicant: TOPNIR SYSTEMS SAS, Aix en Provence (FR)

(72) Inventors: Didier Lambert, Bernos Baeulac (FR); Claude Saint Martin, Pelissane (FR); Miguel Sanchez, Lavera (FR); Bernard Ribero, Peyrolles en Provence (FR); Marc Valleur, Le Chesnay (FR)

(73) Assignee: TOPNIR SYSTEMS SAS, Aix en Provence (FR)

( * ) Notice: Subject to any disclaimer, the term of this patent is extended or adjusted under 35 U.S.C. 154(b) by 0 days.

(21) Appl. No.: 15/318,623

(22) PCT Filed: Jun. 9, 2015

(86) PCT No.: PCT/EP2015/062856
§ 371 (c)(1),
(2) Date: Dec. 13, 2016

(87) PCT Pub. No.: WO2015/189220
PCT Pub. Date: Dec. 17, 2015

(65) Prior Publication Data
US 2017/0131728 A1    May 11, 2017

(30) Foreign Application Priority Data

Jun. 13, 2014    (EP) .................................... 14290172

(51) Int. Cl.
*G01N 33/28*    (2006.01)
*G05D 11/13*    (2006.01)
(Continued)

(52) U.S. Cl.
CPC ......... *G05D 11/139* (2013.01); *G01N 21/359* (2013.01); *G01N 23/223* (2013.01);
(Continued)

(58) Field of Classification Search
CPC ..... G01N 33/28; G01N 21/359; G05D 11/139
See application file for complete search history.

(56) References Cited

U.S. PATENT DOCUMENTS 8,017,910 B2 *  9/2011  Sharpe ................ G01N 21/359
                                                    250/253
8,322,200 B2 * 12/2012  Brown ............... G01N 33/2829
                                                    73/64.56
(Continued)

FOREIGN PATENT DOCUMENTS

EP            0801299 A1    10/1997

OTHER PUBLICATIONS

Espinosa et al., "Use NIR Technology to Optimize Plant Operations", Hydrocarbon Processing, Gulf Publishing Co., Houston, Texas, Feb. 1, 1995, pp. 86-89 and 91-92.
(Continued)

*Primary Examiner* — Ellen M McAvoy
(74) *Attorney, Agent, or Firm* — Maschoff Brennan

(57) ABSTRACT

The invention relates to a method and a device for certifying and optimizing a mixture of components in order to obtain a target product by spectral analysis, preferably by (topological) spectral analysis in the near infra-red ("NIR").

16 Claims, 10 Drawing Sheets

(51) Int. Cl.
*G01N 33/22* (2006.01)
*G01N 23/223* (2006.01)
*G01N 21/359* (2014.01)

(52) U.S. Cl.
CPC ......... *G01N 33/22* (2013.01); *G01N 2201/12* (2013.01); *G01N 2223/304* (2013.01); *G01N 2223/637* (2013.01)

(56) References Cited

U.S. PATENT DOCUMENTS

| | | | | |
|---|---|---|---|---|
| 8,494,818 | B2* | 7/2013 | Hubert | G01N 21/274 703/2 |
| 9,568,461 | B2* | 2/2017 | Von Herzen | F01M 11/10 |
| 9,624,448 | B2* | 4/2017 | Joo | C10L 1/04 |
| 9,651,538 | B2* | 5/2017 | Von Herzen | G01N 33/2888 |
| 9,709,545 | B2* | 7/2017 | Mertens | G01N 33/22 |
| 2009/0158824 | A1 | 6/2009 | Brown et al. | |
| 2012/0279114 | A1 | 11/2012 | Kelly et al. | |
| 2012/0290223 | A1 | 11/2012 | Mertens | |
| 2017/0307582 | A1* | 10/2017 | Mertens | G01N 33/22 |

OTHER PUBLICATIONS

Muradov et al., "Study of absorption spectra of gasolines and other hydrocarbon mixtures in the second overtone region of the CH3, CH2, CH groups", Journal of Applied Spectroscopy, KLUWER Academic Publishers-Plenum Publishers, NE, vol. 74, No. 2, Mar. 1, 2007, pp. 174-179.

* cited by examiner

SPECTRAL DATABASE A

FIGURE 2

| Wave Length VGS | W1 | W2 | W3 | W4 | W5 | W6 | W7 | W8 | W9 |
|---|---|---|---|---|---|---|---|---|---|
| | 1.52455E-07 | 5.98E-06 | 5.43E-06 | 9.39E-06 | 1.38E-05 | 2.07E-05 | 2.62E-05 | 3.04E-05 | 4.14E-05 |
| | 1.12042E-07 | 6.81E-06 | 5.33E-06 | 9.54E-06 | 1.46E-05 | 2.15E-05 | 2.69E-05 | 3.11E-05 | 4.18E-05 |
| | 1.55755E-06 | 4.53E-06 | 6.07E-06 | 9.07E-06 | 1.45E-05 | 2.07E-05 | 2.66E-05 | 3.13E-05 | 4.12E-05 |
| | 4.15098E-08 | 6.65E-06 | 5.33E-06 | 9.63E-06 | 1.45E-05 | 2.09E-05 | 2.62E-05 | 3.12E-05 | 4.14E-05 |
| | 1.28445E-07 | 6.52E-06 | 5.19E-06 | 9.68E-06 | 1.46E-05 | 2.21E-05 | 2.7E-05 | 3.08E-05 | 4.2E-05 |
| | 1.52686E-06 | 4.24E-06 | 6.16E-06 | 8.66E-06 | 1.36E-05 | 1.97E-05 | 2.57E-05 | 3.07E-05 | 4.05E-05 |
| | 1.45709E-06 | 4.02E-06 | 6.06E-06 | 9.18E-06 | 1.47E-05 | 2.04E-05 | 2.63E-05 | 3.14E-05 | 4.1E-05 |
| | 1.8449E-06 | 4.52E-06 | 5.79E-06 | 8.99E-06 | 1.43E-05 | 2.00E-05 | 2.62E-05 | 3.16E-05 | 4.17E-05 |
| | 1.73044E-06 | 4.4E-06 | 6.12E-06 | 8.94E-06 | 1.42E-05 | 2.04E-05 | 2.63E-05 | 3.11E-05 | 4.07E-05 |
| | 1.11909E-06 | 3.85E-06 | 6.37E-06 | 9.31E-06 | 1.43E-05 | 2.08E-05 | 2.59E-05 | 3.07E-05 | 4.07E-05 |
| VGSm | 9.6703E-07 | 5.15E-06 | 5.79E-06 | 9.24E-06 | 1.43E-05 | 2.07E-05 | 2.63E-05 | 3.11E-05 | 4.12E-05 |
| σ | 7.6254E-07 | 1.19E-06 | 4.27E-07 | 3.31E-07 | 3.79E-07 | 6.75E-07 | 4.21E-07 | 3.79E-07 | 4.99E-07 |
| $\frac{\sigma}{m} \times 100$ | 78.85 | 23.09 | 7.38 | 3.58 | 2.65 | 3.26 | 1.60 | 1.22 | 1.21 |

SPECTRAL DATABASE B

IMPROVED SPECTRAL DATABASE A'

| Absorbance Name | %Weight | Germ 1 | Germ 2 | Germ 3 | 4764 | 4760 | 4756 | 4752 | 4748 | 4744 | 4740 | 4736 |
|---|---|---|---|---|---|---|---|---|---|---|---|---|
| A0000001 | | | | | 7.79E-06 | 1.29E-05 | 1.88E-05 | 2.42E-05 | 3.16E-05 | 4.42E-05 | 6.18E-05 | 8.01E-05 |
| A0000002 | | | | | 8.08E-06 | 1.37E-05 | 1.99E-05 | 2.5E-05 | 3.18E-05 | 4.46E-05 | 6.09E-05 | 7.91E-05 |
| A0000003 | | | | | 8.78E-06 | 1.52E-05 | 2.23E-05 | 2.97E-05 | 3.99E-05 | 5.53E-05 | 7.54E-05 | 9.68E-05 |
| A0000004 | | | | | 7.46E-06 | 1.26E-05 | 1.81E-05 | 2.47E-05 | 3.29E-05 | 4.71E-05 | 6.55E-05 | 8.47E-05 |
| A0000005 | | | | | 1.01E-05 | 1.59E-05 | 2.39E-05 | 3.28E-05 | 4.34E-05 | 5.93E-05 | 8.09E-05 | 0.000104 |
| A0000006 | | | | | 5.49E-06 | 9.2E-06 | 1.41E-05 | 1.88E-05 | 2.54E-05 | 3.62E-05 | 5.18E-05 | 6.97E-05 |
| A0000007 | | | | | 7.14E-06 | 1.21E-05 | 1.86E-05 | 2.41E-05 | 3.27E-05 | 4.63E-05 | 6.52E-05 | 8.49E-05 |
| A0000008 | | | | | 1.03E-05 | 1.64E-05 | 2.4E-05 | 3.26E-05 | 4.39E-05 | 6.13E-05 | 8.42E-05 | 0.000109 |
| A0000009 | | | | | 8.25E-06 | 1.15E-05 | 1.4E-05 | 1.62E-05 | 1.99E-05 | 2.56E-05 | 3.56E-05 | 4.94E-05 |
| 12G022 | 0.564 | A0000003 | A0000006 | | 7.35E-06 | 1.26E-05 | 1.88E-05 | 2.49E-05 | 3.35E-05 | 4.7E-05 | 6.51E-05 | 8.5E-05 |
| | 0.436 | | | | | | | | | | | |
| 12G011 | 0.654 | A0000009 | A0000001 | | 8.09E-06 | 1.2E-05 | 1.57E-05 | 1.9E-05 | 2.4E-05 | 3.21E-05 | 4.47E-05 | 6E-05 |
| | 0.346 | | | | | | | | | | | |
| 12G036 | 0.44 | A0000008 | A0000004 | | 8.69E-06 | 1.43E-05 | 2.07E-05 | 2.81E-05 | 3.77E-05 | 5.33E-05 | 7.30E-05 | 9.54E-05 |
| | 0.56 | | | | | | | | | | | |
| 13G038 | 0.747 | A0000008 | A0000002 | A0000004 | 9.71E-06 | 1.57E-05 | 2.29E-05 | 3.06E-05 | 4.09E-05 | 5.7E-05 | 7.83E-05 | 0.000101 |
| | 0.258 | | | | | | | | | | | |
| | -0.005 | | | | | | | | | | | |
| 13G025 | 0.5825 | A0000008 | A0000005 | A0000003 | 1E-05 | 1.61E-05 | 2.38E-05 | 3.23E-05 | 4.33E-05 | 6E-05 | 8.22E-05 | 0.000106 |
| | 0.3020 | | | | | | | | | | | |
| | 0.1155 | | | | | | | | | | | |
| 13G019 | 0.094 | A0000004 | A0000005 | A0000007 | 7.43E-06 | 1.25E-05 | 1.81E-05 | 2.46E-05 | 3.28E-05 | 4.7E-05 | 6.54E-05 | 8.46E-05 |
| | -0.00047 | | | | | | | | | | | |
| | 0.00647 | | | | | | | | | | | |

ENLARGED SPECTRAL DATABASE E

FIGURE 5

| Absorbance | Pole | Germ | %Weight | 4764 | 4760 | 4756 | 4752 | 4748 | 4744 | 4740 | 4736 | 4732 |
|---|---|---|---|---|---|---|---|---|---|---|---|---|
| Name | | | | | | | | | | | | |
| A0000001 | | | | 7.78E-06 | 1.29E-05 | 1.88E-05 | 2.42E-05 | 3.16E-05 | 4.42E-05 | 6.18E-05 | 8.01E-05 | 9.88E-05 |
| A0000002 | | | | 8.08E-06 | 1.37E-05 | 1.96E-05 | 2.5E-05 | 3.18E-05 | 4.46E-05 | 6.09E-05 | 7.91E-05 | 9.8E-05 |
| A0000003 | | | | 8.78E-06 | 1.52E-05 | 2.23E-05 | 2.97E-05 | 3.99E-05 | 5.53E-05 | 7.54E-05 | 9.68E-05 | 0.000118 |
| A0000004 | | | | 7.46E-06 | 1.26E-05 | 1.81E-05 | 2.47E-05 | 3.29E-05 | 4.71E-05 | 6.55E-05 | 8.47E-05 | 0.000104 |
| A0000005 | | | | 1.01E-05 | 1.59E-05 | 2.39E-05 | 3.28E-05 | 4.34E-05 | 5.93E-05 | 8.08E-05 | 0.000104 | 0.000128 |
| A0000006 | | | | 5.49E-06 | 9.2E-06 | 1.41E-05 | 1.88E-05 | 2.54E-05 | 3.62E-05 | 5.18E-05 | 6.97E-05 | 8.68E-05 |
| A0000007 | | | | 7.14E-06 | 1.21E-05 | 1.86E-05 | 2.41E-05 | 3.27E-05 | 4.63E-05 | 6.52E-05 | 8.49E-05 | 0.000104 |
| A0000008 | | | | 1.03E-05 | 1.64E-05 | 2.4E-05 | 3.26E-05 | 4.39E-05 | 6.13E-05 | 8.42E-05 | 0.000109 | 0.000136 |
| A0000009 | | | | 8.25E-06 | 1.15E-05 | 1.4E-05 | 1.62E-05 | 1.99E-05 | 2.56E-05 | 3.56E-05 | 4.94E-05 | 6.62E-05 |
| MEG001 | PAL054 | A0000009 | 0.15 | 4.45E-06 | 7.13E-06 | 9.35E-06 | 1.12E-05 | 1.44E-05 | 1.95E-05 | 2.84E-05 | 4.08E-05 | 5.62E-05 |
| MEG002 | PAL014 | A0000005 | -0.05 | 1.15E-05 | 1.78E-05 | 2.63E-05 | 3.57E-05 | 4.69E-05 | 6.36E-05 | 8.61E-05 | 0.00011 | 0.000135 |
| MEG003 | PAL035 | A0000008 | 0.08 | 8.11E-06 | 1.37E-05 | 2.06E-05 | 2.84E-05 | 3.88E-05 | 5.48E-05 | 7.6E-05 | 9.89E-05 | 0.000124 |
| MEG004 | PRF006 | A0000002 | 0.021655 | 8.65E-06 | 1.43E-05 | 2.03E-05 | 2.57E-05 | 3.26E-05 | 4.53E-05 | 6.16E-05 | 7.98E-05 | 9.88E-05 |
| MEG005 | PRF004 | A0000007 | -0.07268 | 4.86E-06 | 9.48E-06 | 1.56E-05 | 2.07E-05 | 2.94E-05 | 4.35E-05 | 6.29E-05 | 8.26E-05 | 0.000102 |
| MEG006 | PRF074 | A0000003 | 0.028752 | 9.54E-06 | 1.61E-05 | 2.33E-05 | 3.07E-05 | 4.07E-05 | 5.59E-05 | 7.58E-05 | 9.72E-05 | 0.000119 |

ENLARGED SPECTRAL DATABASE EE

FIGURE 6

| Absorbance Name | Germ 1 | Germ 2 | Germ 3 | pole | %Weight | 4764 | 4760 | 4756 | 4752 | 4748 | 4744 | 4740 |
|---|---|---|---|---|---|---|---|---|---|---|---|---|
| A00000001 | | | | | | 7.78E-06 | 1.29E-05 | 1.88E-05 | 2.42E-05 | 3.16E-05 | 4.42E-05 | 6.18E-05 |
| A00000002 | | | | | | 8.08E-06 | 1.37E-05 | 1.96E-05 | 2.5E-05 | 3.18E-05 | 4.46E-05 | 6.09E-05 |
| A00000003 | | | | | | 8.78E-06 | 1.52E-05 | 2.23E-05 | 2.97E-05 | 3.99E-05 | 5.53E-05 | 7.54E-05 |
| A00000004 | | | | | | 7.46E-06 | 1.26E-05 | 1.81E-05 | 2.47E-05 | 3.29E-05 | 4.71E-05 | 6.55E-05 |
| A00000005 | | | | | | 1.01E-05 | 1.59E-05 | 2.39E-05 | 3.28E-05 | 4.34E-05 | 5.93E-05 | 8.08E-05 |
| A00000006 | | | | | | 5.49E-06 | 9.2E-06 | 1.41E-05 | 1.89E-05 | 2.54E-05 | 3.62E-05 | 5.18E-05 |
| A00000007 | | | | | | 7.14E-06 | 1.21E-05 | 1.86E-05 | 2.41E-05 | 3.27E-05 | 4.63E-05 | 6.52E-05 |
| A00000008 | | | | | | 1.03E-05 | 1.64E-05 | 2.4E-05 | 3.26E-05 | 4.39E-05 | 6.13E-05 | 8.42E-05 |
| A00000009 | | | | | | 8.25E-06 | 1.15E-05 | 1.4E-05 | 1.62E-05 | 1.99E-05 | 2.56E-05 | 3.56E-05 |
| MEP001 | A00000002 | A00000006 | | 0 | PAL031 0.56 / 0.34 / 0.1 0.304 / 0.646 / | 4.86E-06 | 8.85E-06 | 1.35E-05 | 1.8E-05 | 2.41E-05 | 3.54E-05 | 5.04E-05 |
| MEP002 | A00000005 | A00000003 | | 0 | PRF028 0.05 1.1726 / -0.0926 | 1.05E-05 | 1.68E-05 | 2.45E-05 | 3.24E-05 | 4.26E-05 | 5.78E-05 | 7.8E-05 |
| MEP003 | A00000005 | A00000008 | | 0 | PRF063 / -0.08 0.306 / -0.0530 / | 8.68E-06 | 1.44E-05 | 2.21E-05 | 3.1E-05 | 4.19E-05 | 5.78E-05 | 7.97E-05 |
| MEP004 | A00000006 | A00000009 | A00000002 | PAL037 | 0.647 / 0.1 0.6062 / 0.314 / | 4.89E-06 | 9.38E-06 | 1.46E-05 | 1.93E-05 | 2.55E-05 | 3.67E-05 | 5.17E-05 |
| MEP005 | A00000008 | A00000005 | A00000003 | PAL006 | 0.1198 / -0.04 0.273 / 0.4170 / | 1.11E-05 | 1.76E-05 | 2.56E-05 | 3.44E-05 | 4.59E-05 | 6.33E-05 | 8.63E-05 |
| MEP006 | A00000002 | A00000006 | A00000005 | PRF025 | 0.22 / 0.09 | 9.96E-06 | 1.52E-05 | 2.16E-05 | 2.8E-05 | 3.54E-05 | 4.75E-05 | 6.44E-05 |

ENLARGED SPECTRAL DATABASE EE1

FIGURE 7

| Name | Kcy | Ksatu | Karo | Kiso | Kene | xxxx |
|---|---|---|---|---|---|---|
| CRK0071 | 124.2982 | 30.2213 | 6.1022 | 20.4044 | 22.6714 | |
| CRK0075 | 123.6416 | 30.3821 | 6.0959 | 20.0519 | 22.6293 | |
| CRK0098 | 123.3631 | 29.719 | 6.1168 | 21.0968 | 22.9267 | |
| CRK0102 | 122.6272 | 29.1777 | 6.1166 | 20.8441 | 23.3606 | |
| CRK0116 | 120.3105 | 29.5099 | 6.1134 | 21.0583 | 23.0629 | |
| HVY0068 | 144.4259 | 52.0212 | 5.9475 | 22.2027 | 13.5996 | |
| HVY0088 | 141.8204 | 47.8997 | 6.0091 | 23.0564 | 14.2034 | |
| HVY0093 | 143.0184 | 49.2953 | 5.9834 | 22.8627 | 14.0157 | |
| HVY0100 | 142.1157 | 48.486 | 5.9932 | 22.8486 | 14.183 | |
| HVY0106 | 143.3684 | 50.5179 | 5.9642 | 22.8179 | 13.8181 | |
| KER0072 | 114.2108 | 61.7041 | 5.8061 | 22.7724 | 13.9045 | |
| KER0076 | 112.7754 | 59.6154 | 5.8289 | 23.7607 | 14.191 | |
| KER0079 | 113.9782 | 56.389 | 5.8964 | 22.7878 | 14.299 | |
| KER0080 | 113.2538 | 57.5513 | 5.8681 | 23.0583 | 14.2554 | |
| KER0082 | 114.2399 | 62.3519 | 5.8108 | 23.6506 | 13.8976 | |
| LGT0067 | 130.8834 | 53.1217 | 5.9227 | 22.969 | 13.9002 | |
| LGT0087 | 129.4485 | 49.2411 | 5.9723 | 23.7952 | 14.4472 | |
| LGT0096 | 129.5462 | 48.6752 | 5.9809 | 23.382 | 14.5025 | |
| LGT0099 | 129.1717 | 48.8969 | 5.9775 | 23.6349 | 14.5186 | |
| LGT0105 | 129.4355 | 50.1752 | 5.9592 | 23.4217 | 14.267 | |

TABLE OF AGGREGATES

FIGURE 9

| Absorbance Ncm | %Poids | Germe 1 | Germe 2 | Germe 3 | 4764 | 4760 | 4756 | 4752 | 4748 | 4744 | 4740 | 4736 | 4732 | MON | RON |
|---|---|---|---|---|---|---|---|---|---|---|---|---|---|---|---|
| A00000001 | | | | | 7.78E-06 | 1.29E-05 | 1.88E-05 | 2.42E-05 | 3.16E-05 | 4.42E-05 | 6.18E-05 | 8.01E-05 | 9.85E-05 | 85.1 | 94.2 |
| A00000002 | | | | | 8.08E-06 | 1.37E-05 | 1.96E-05 | 2.5E-05 | 3.18E-05 | 4.46E-05 | 6.09E-05 | 7.91E-05 | 9.8E-05 | 85.3 | 94.7 |
| A00000003 | | | | | 8.78E-06 | 1.52E-05 | 2.23E-05 | 2.97E-05 | 3.99E-05 | 5.53E-05 | 7.54E-05 | 9.68E-05 | 0.000119 | 85 | 94 |
| A00000004 | | | | | 7.46E-06 | 1.26E-05 | 1.81E-05 | 2.47E-05 | 3.29E-05 | 4.71E-05 | 6.55E-05 | 8.47E-05 | 0.000104 | 85 | 93.5 |
| A00000005 | | | | | 1.01E-05 | 1.59E-06 | 2.39E-05 | 3.28E-05 | 4.34E-05 | 5.93E-05 | 8.08E-05 | 0.000104 | 0.000128 | 85.3 | 95.1 |
| A00000006 | | | | | 5.49E-06 | 9.2E-06 | 1.41E-05 | 1.88E-05 | 2.54E-05 | 3.62E-05 | 5.38E-05 | 6.97E-05 | 8.68E-05 | 84.4 | 92.8 |
| A00000007 | | | | | 7.14E-06 | 1.23E-05 | 1.85E-05 | 2.41E-05 | 3.27E-05 | 4.63E-05 | 6.52E-05 | 8.45E-05 | 0.000104 | 85 | 93.5 |
| A00000008 | | | | | 1.03E-05 | 1.64E-05 | 2.4E-05 | 3.28E-05 | 4.35E-05 | 6.13E-05 | 8.42E-05 | 0.000109 | 0.000136 | 85.5 | 95.1 |
| A00000009 | | | | | 8.25E-06 | 1.15E-05 | 1.4E-05 | 1.62E-05 | 1.99E-05 | 2.56E-05 | 3.56E-05 | 4.54E-05 | 6.02E-05 | 85.4 | 95 |
| 12G022 | 0.564 | A00000003 | A00000006 | | 7.35E-06 | 1.26E-06 | 1.88E-05 | 2.49E-05 | 3.36E-05 | 4.7E-05 | 6.51E-05 | 8.5E-05 | 0.000105 | 84.73846 | 93.47693 |
| | 0.436 | | | | | | | | | | | | | | |
| 12G011 | 0.654 | A00000009 | A00000001 | | 8.09E-06 | 1.2E-05 | 1.57E-05 | 1.9E-05 | 2.4E-05 | 3.21E-05 | 4.47E-05 | 6E-05 | 7.75E-05 | 85.39608 | 94.72297 |
| | 0.346 | | | | | | | | | | | | | | |
| 12G036 | 0.44 | A00000008 | A00000004 | | 8.69E-06 | 1.43E-06 | 2.07E-05 | 2.81E-05 | 3.77E-05 | 5.33E-05 | 7.38E-05 | 9.54E-05 | 0.000118 | 85.21994 | 94.20381 |
| | 0.56 | | | | | | | | | | | | | | |
| 13G038 | 0.747 | A00000008 | A00000002 | A00000004 | 9.71E-06 | 1.57E-05 | 2.29E-05 | 3.06E-05 | 4.09E-06 | 5.7E-05 | 7.83E-05 | 0.000101 | 0.000126 | 85.45096 | 95.00502 |
| | 0.258 | | | | | | | | | | | | | | |
| | -0.005 | | | | | | | | | | | | | | |
| 13G035 | 0.5825 | A00000008 | A00000005 | A00000003 | 1E-05 | 1.61E-05 | 2.38E-05 | 3.23E-05 | 4.33E-05 | 6E-05 | 8.22E-05 | 0.000106 | 0.000131 | 85.38181 | 94.97284 |
| | 0.3020 | | | | | | | | | | | | | | |
| | 0.1155 | | | | | | | | | | | | | | |
| 13G019 | 0.094 | A00000004 | A00000005 | A00000007 | 7.43E-06 | 1.25E-05 | 1.81E-05 | 2.46E-05 | 3.28E-05 | 4.7E-05 | 6.54E-05 | 8.46E-05 | 0.000104 | 84.99859 | 93.49345 |
| | -0.000847 | | | | | | | | | | | | | | |
| | 0.8647 | | | | | | | | | | | | | | |

ENLARGED SPECTRAL DATABASE E - with characterization

FIGURE 10

METHOD OF PREPARING A CERTIFIED TARGET PRODUCT FROM A MIXTURE OF COMPONENTS BY SPECTRAL ANALYSIS

This invention relates to a method and certification and optimization device of a mixture of components to obtain a target product by spectral analysis, preferably by near infrared ("NIR") (topological) spectral analysis.

In particular, this invention relates to the regulation of mixtures of the components by batch or on line, such as for example, petroleum product mixtures or others, in which said mixtures are in accordance with a set of significant specifications.

More in particular, this invention relates to a method and certification and optimization device of a mixture of components for obtaining a target product by spectral analysis, for example by NMR, Raman, IR, and/or UV/Visible, preferably by near infrared ("NIR") (topological) spectral analysis, under constraint, said constraint being based
- on the preferred use of at least one of the components of the mixture, and/or
- on the modification of at least one characteristic of the target product.

When a mixture of various components, the objective is to obtain a target product with a range of values having predetermined physical-chemical characteristics enabling the ability to be certified. By way of example, for a mixture of petroleum products, for example, a fuel, these characteristics may be its octane rating, its cetane index, its resistance to cold, the polyaromatic compound content, the vapor pressure, etc.

The present invention will apply in particular to the mixing of components of target petroleum products (for example fuels) in any suitable place, for example a refinery, an oil depot and/or any device using a petroleum product consisting of a mixture of components prepared by batch and/or online.

Thus, in a petroleum depot and/or an oil refinery, motor fuels can be produced by the so-called batch and/or in-line mixing technique, in which the various liquid components and any additives are introduced in a tank and/or a line serving as a mixer.

This introduction of the various components may be carried out simultaneously or not. This mixture of various components may be performed by batch and/or continuously. The flow of the various components and/or the concentration of the various components are generally ordered and controlled by a computer and the preparation time of a fuel lot may take several dozens of hours.

It is to this type of industrial plant that reference will be made more precisely in the remainder of this description, without this implying a limitation of the scope of application of the invention. The properties of the manufactured target product (for example, a fuel) are repeatedly checked during manufacture and analyzes are carried out for this purpose on samples taken from the mixer and/or in the storage enclosure during filling. From the results of these analyzes, the flow rates and/or the concentrations of the components of the mixture as well as any additives are adjusted to align the measured values with the set values. For each analysis, it is advantageous to minimize the time interval between the taking of a sample of the mixture being prepared and obtaining the measured value; although "on-line" analyzers can theoretically meet this need, it has been found that rapid changes in the components and the characteristics of the target products do not always make it possible to be fully effective and that it was still often necessary to sample and carry out the analyzes "off-line".

Indeed, a particularity of the components mixed for the preparation of the target products is that they can either originate from different supply sources and/or simply vary in terms of quality and/or physico-chemical characteristics over time. This feature has become all the more critical in recent years because of the effects of globalization and the multiplicity of access to new supply sources. Therefore, there is a need in the art for having an improved means of preparing petroleum products which more effectively meets these new requirements.

Another characteristic of the target petroleum products has also emerged in recent years. Environmental changes have led to the adoption of new standards and/or permanent changes in certain characteristics of the target petroleum products. An example may be mentioned of the temporary production of less polluting fuels during pollution peaks and/or the content of the bio-components of said fuels.

Therefore, there is a need in the art for having an improved means of preparing and certifying petroleum products which more effectively meets these new requirements.

It is these problems that this invention proposes to solve by using a method and/or device for certification and optimization of a mixture of components for obtaining a target product by spectral analysis, for example by NMR, Raman, IR, NIR and/or UV/Visible, preferably by near infrared ("NIR") (topological) spectral analysis.

In particular, this invention relates to the regulation of mixtures of the constituents by batch and/or on line, such as for example, petroleum product mixtures, in which said mixtures are in accordance with a set of significant specifications.

More particularly, this invention relates to a method and a device for certification and optimization of a mixture of components for obtaining a target product by spectral analysis, for example by NMR, Raman, IR, NIR and/or UV/Visible, preferably by near-infrared ("NIR") (topological) spectral analysis under constraint, said constraint being based
- on the preferred use of at least one of the components of the mixture, and/or
- modifying at least one characteristic of the target product and/or
- improving at least one property of the target product, said property being part of the certification conditions of said target product.

Process M

Thus, this invention relates to a process M for certification and preparation of a target product, for example a target petroleum product for example a fuel, by batch and/or in-line mixing of its "n" components from different flows from said components at controlled concentrations and/or flow rates, with optional incorporation of additives, said target product having to be marketed with a set of ranges of physico-chemical characteristic values, method in which a batch and/or continuous mixer is fed said components at controlled concentrations and/or flow rates, said process being characterized in that:
1. there is at least one spectral datum characterizing the target product and which defines its spectral range, the value of said spectral datum satisfying at least one condition of the certification process,
2. spectral datum (data) is (are) available, each individually characterizing at least two—preferably all the "n"-components of the target product, 3. a computer program is used which makes it possible to calculate the ranges of respective proportions of said components necessary for reconstituting a spectral datum of the mixture belonging to the spectral range of Step 1 from the spectral datum (data) of Step 2, and
4. the ranges of respective proportions of the constituents of step 3 are used to control the concentrations and/or flow rates of the components fed into the mixer so as to prepare the target product whose value of said spectral datum satisfies the same condition (or same conditions) of the certification process of the first Step.

According to one embodiment of this invention, the value of said spectral datum of the target product thus prepared is obtained by calculation during Step 3 during reconstitution of the spectral mixing datum.

According to one embodiment of this invention, the value of said spectral datum of the target product thus prepared is obtained by spectral measurement of the product thus obtained.

According to one embodiment of this invention, the value of said spectral datum of the target product thus prepared is obtained both by calculation during Step 3 during reconstitution of the spectral mixing datum, and also by spectral measurement of the product thus obtained.

This invention is therefore characterized by the fact that at least one spectral datum characterizing the target product is available and which defines its spectral range, the value of said spectral datum responding to at least one condition of the certification process. These spectral data are preferably data measured by the same type of spectral analysis, preferably using the same type of spectrometer, these spectral data may for example be "spectra".

The target product according to this invention must therefore possess for marketing purposes a set of ranges of values of physico-chemical characteristics which are dictated by the certification process; these ranges of values of physico-chemical characteristics are generally defined by means of ranges of target product "properties", examples of said properties being defined in greater detail in the remainder of this description. Thus, in one embodiment of this invention, one condition of the certification process may advantageously mean a range of values of a property "X" of the target product, said property "X" being part of the properties required by the Certification process for the target product; thus, in this embodiment, the value of the spectral datum of Step 1 corresponds to a value of the property "X" which itself satisfies a condition of the certification process. This invention therefore allows spectral data to not only control the concentrations and/or flow rates of the components fed into the mixer so as to prepare the target product but also to ensure that the target product satisfies the conditions/constraints of the Certification process.

Process M1—Spectrum

Thus, this invention also relates to a process M1 for certification and preparation of a target product, for example a target petroleum product, for example a fuel, by batch and/or in-line mixing of its "n" components from different flows from said components at controlled concentrations and/or flow rates, with optional incorporation of additives, said target product having to be marketed with a set of ranges of physico-chemical characteristic values, method in which a batch and/or continuous mixer is fed said components at controlled concentrations and/or flow rates, said process being characterized in that:
1. there is at least one analysis spectrum characterizing the target product and which defines its spectral range, the characteristics of said analysis spectrum meeting at least one condition of the certification process,
2. the analysis spectrum (spectra) is available, each individually characterizing at least two—preferably all the "n"-components of the target product,
3. a computer program is used which makes it possible to calculate the ranges of respective proportions of said components necessary for reconstituting from a mixing spectrum belonging to the spectral range of Step 1 from the spectrum (spectra) of the components of Step 2, and
4. the ranges of the respective proportions of the components of Step 3 are used to control the concentrations and/or flow rates of the components feeding the mixer so as to prepare the target product whose spectrum satisfies the same condition (or the same conditions) of the first Step of the certification process.

According to one embodiment of this invention, tire spectrum of the target product thus prepared is obtained by calculation in Step 3 during reconstitution of the mixing spectrum.

According to one embodiment of this invention, the spectrum of the target product thus prepared is obtained by spectral measurement of the product thus obtained.

According to one embodiment of this invention, the spectrum of the target product thus prepared is obtained both by calculation in Step 3 during reconstitution of the mixing spectrum and also by spectral measurement of the product thus obtained.

The spectral range characterizing the target product can be determined by any suitable method. By way of example, this field will be determined by means of the aggregates as described hereinafter in the description. The fundamental characteristic of the spectral range is that it defines the fact that the final mixture conforms to a set of significant specifications of the target product; this is what makes it possible to say that the mixture is on spec ("on-spec" in the English language) according to the jargon used by a person skilled in the art.

The target product (e.g., a petroleum product) generally contains a major component whose concentration by weight in the target product is the highest. According to a particular and preferred embodiment of this invention, at least one of the spectra characterizing one of the minor components (that is to say any non-major components) of the target product of the aforementioned Step 2 is a spectrum obtained by analyzing a mixture of said minor component with either said major component or a representative mixture of the target product.

According to one embodiment of this invention, the number of components "n" of the target product is greater than or equal to two, for example greater than or equal to three.

As already indicated, the spectral data are preferably data measured by means of the same type of spectral analysis, preferably using the same type of spectrometer, these spectral data may for example be any appropriate type of spectral quantities constituting a corresponding spectral database. These spectral quantities may be any type of signals characterizing the spectra, for example the absorbances, transmittances, reflectances, etc.; the optical absorbances or densities being the most commonly used signals.

By way of example, we may also mention as signals the derivatives of the absorbances or any other measurement resulting from another type of mathematical processing of said absorbances.

This invention is therefore characterized by having at least one spectrum characterizing the target product and defining its spectral range, said spectrum responding to at least one condition of the certification process. These spectra are preferably data measured by the same type of spectral analysis, preferably using the same type of spectrometer.

The target product according to this invention must therefore possess a set of ranges of values of physico-chemical characteristics for marketing purposes which are dictated by the certification process; these ranges of values of physico-chemical characteristics are generally defined by means of ranges of "properties" of the target product, examples of said properties being defined in greater detail in the remainder of this description. Thus, in one embodiment of this invention, a condition of the certification process can advantageously mean a range of values of a property "X" of the target product, said property "X" being part of the properties required by the certification process for the target product; thus, in this embodiment, the spectrum of Step 1 corresponds to a value of the property "X" which itself satisfies a condition of the certification process. This invention therefore makes it possible by means of the spectrum to not only control the concentrations and/or flow rates of the components fed into the mixer so as to prepare the target product but also to ensure that the target product satisfies the conditions/constraints of the Certification process.

According to one embodiment of this invention, the spectral data constitute one (or tore) spectral databases.

Process M2—Spectral Database

Thus, according to a particular embodiment, the present invention also relates to a M2 Process for certifying and preparing a target product, for example a petroleum target product, for example a fuel, by batch and/or online mixing of its "n" components from different flows of said components in concentrations and/or controlled flow rates, with an optional incorporation of additives, said target product requiring a set of ranges of values of physico-chemical characteristics to be marketed, method in winch a batch and/or continuous mixer is fed with said components at controlled concentrations and/or flow rates, said method being characterized in that:

1. there is a spectral database characterizing the target product and defining its spectral range, said spectral database meeting at least one condition of the certification process.
2. a spectral database is available, each individually characterizing at least two—preferably all the "n"—components of the target product,
3. a computer program is used to calculate the ranges of the respective proportions of said components necessary for the reconstitution, from the spectral databases of Step 2, of a spectral mixing database belonging to the spectral range of the Step 1.
4. the ranges of respective proportions of the constituents of step 3 are used to control the concentrations and/or flow rates of the components fed into the mixer so as to prepare the target product whose spectral database satisfies the same condition (or same conditions) of the certification process of the first Step.

According to one embodiment of this invention, the spectral database of the target product thus prepared is obtained by calculation during Step 3 during reconstitution of the spectral mixing database.

According to one embodiment of this invention, the spectral database of the target product thus prepared is obtained by spectral measurement of the target product thus obtained.

According to one embodiment of this invention, the spectral database of the target product thus prepared is obtained both by calculation during Step 3 during reconstitution of the spectral mixing database, and also by spectral measurement of the product thus obtained.

The spectral range characterizing the target product can be determined by any suitable method. By way of example, this field will be determined by means of the aggregates as described hereinafter in the description. The fundamental characteristic of the spectral domain is that it defines the fact that the final mixture conforms to a set of significant specifications of the target product; this is what makes it possible to say that the mixture is on spec ("on-spec" in the English language) according to the jargon used by a person skilled in the art.

According to one particular embodiment of this invention, after the second step, from the spectral databases of the components, 2a spectral databases are formed which characterize the mixtures of said components and which are used for Step 3.

Process M2a

Thus, according to one particular embodiment, this invention also relates to a process M2a for certification and preparation of a target product, for example a target petroleum product, for example a fuel, by batch and/or in-line mixing of its components from different flows of said components at controlled concentrations and/or flow rates, with optional incorporation of additives, said target product having to be marketed with a set of ranges of physico-chemical characteristic values, method in which a batch and/or continuous mixer is fed said components at controlled concentrations and/or flow rates, said process being characterized in that:

1. there is a spectral database characterizing the target product and defining its spectral range, said spectral database meeting at least one condition of the certification process.
2. a spectral database is available, each individually characterizing at least two—preferably all the "n"—components of the target product,
2a. from the spectral databases of the Step 2 components, spectral databases (2a) which characterize the mixtures of these components are formed,
3. a computer program is used to identify in the spectral databases of step 2a the spectral database(s) of the mixture belonging to the spectral domain of Step 1 and thus making it possible to define the ranges of the respective proportions of the components,
4. the ranges of the respective proportions of the components of Step 3 are used to control the concentrations and/or flow rates of the components fed into the mixer so as to prepare the target product whose spectral database satisfies the same condition (or same conditions) of the certification process of the first Step.

As described above, the spectral range characterizing the target product may be determined by any appropriate method. By way of example, this field will be determined by means of the aggregates as described hereinafter in the description. The fundamental characteristic of the spectral domain is that it defines the fact that the final mixture conforms to a set of significant specifications of the target product; this is what makes it possible to say that the mixture is on spec ("on-spec" in the English language) according to the jargon used by a person skilled in the art.

This invention is therefore characterized by the fact that at least one spectral database characterizing the target product is available and which defines its spectral range, the spectral database responding to at least one condition of the certification process. This spectral database preferably comes from measurements carried out by means of the same type of spectral analysis, preferably by means of the same type of spectrometer.

The target product according to this invention must therefore possess a set of ranges of values of physico-chemical characteristics for marketing purposes which are dictated by the certification process; these ranges of values of physico-chemical characteristics are generally defined by means of ranges of "properties" of the target product, examples of said properties being defined in greater detail in the remainder of this description. Thus, in one embodiment of this invention, a condition of the certification process can advantageously mean a range of values of a property "X" of the target product, said property "X" being part of the properties required by the certification process for the target product; thus, in this embodiment, the spectral database from Step 1 corresponds to a value of the property "X" which itself satisfies a condition of the certification process. This invention thus makes it possible, by means of the spectral databases, not only to control the concentrations and/or flow rates of constituents fed into the mixer so as to prepare the target product but also to ensure that the target product satisfies the conditions/constraints of the Certification process.

As already described above, the target product (e.g., a petroleum product) generally contains a major component whose concentration by weight is the highest in the target product.

According to one particular and preferred embodiment of this invention, at least one of the spectral databases characterizing one of the minor components of the target product of the aforementioned Step 2 is a spectral database obtained by analysis of a mixture of said minor component (i.e., any non-major component) with either said major component or a representative mixture of the target product.

According to one preferred embodiment of this invention, the spectral analysis method used is chosen from, for example, NMR, Raman, IR, NIR and/or UV/Visible, preferably by topological spectral analysis in the near infrared ("NIR").

According to one preferred embodiment of this invention, the certification and preparation process of a target product for on-line mixture of its components which also make it possible to take into account a set of new constraints and thus to optimize said process.

The Applicant has proven that the use of spectral analysis as described above and in particular the use of near-infrared spectral analysis has greatly improved the reliability and above all the response time of the processes for certification and preparation of the target products.

The numerous advantages of this invention will now be described by way of a practical case; said practical case is purely illustrative, which means that what is described hereinafter does not limit the scope of this invention scope of which is defined by the Claims.

Let us take as a target product an SP98 type gasoline, also known as a premium unleaded gasoline. In view of its marketing, this gasoline must therefore possess a set of ranges of values of physico-chemical characteristics which are dictated by the certification process; these ranges of values of physico-chemical characteristics are generally defined by means of the ranges of "properties" [Px] of the target product, examples of said properties [Px] being defined below (it is evident that these properties can evolve over time, depending on the country, the seasons (summer, winter), or also according to the evolution of the raw materials, fuels, additives or even the engines):

P1=Reid Vapor Pressure ["Reid Vapor Pressure (RVP)"] with maximum values that should not be exceeded (example of size "kPa"; examples of maximum value: 60 kPa in summer, 90 kPa in winter). This property is a measure of the volatility of gasoline. This is important because it impacts the operation of vehicles with gasoline engines. For example, high levels of vaporization are desirable for start-up and winter operation, while minimal levels are desirable during summer heat. Thus, oil refineries and/or petroleum terminals and/or fuel terminals manipulate the seasonal Reid vapor pressure to maintain the reliability of the gasoline engine;

P2=volume weight (or density) the value of which must be within a range defined by the current certification (example of dimension "Kg/m3", examples of range: 720-775);

P3=distillation property—percentage evaporated at 70° C. ("E70") with maximum values which should not be exceeded (examples of maximum value: 48% Max. vol. in summer, 50% Max. vol. in winter):

P4=Motor Octane Number (Motor Octane Number "MON") with minimum values (example Min 87.0);

P5=Research Octane Number (Research Octane Number "RON") with minimum values (example Min 95.0);

P6=Benzene content with maximum values which should not be exceeded (example 1% Max. vol.);

P7=olefin content with maximum values which should not be exceeded (example 18% Max. vol.);

P8=Aromatic content with maximum values which should not be exceeded (example 35% Max. vol.);

P9=Oxygen content with maximum values which should not be exceeded (example 2.7% Max. vol.);

P10=Ether content with maximum values which should not be exceeded (example 22% Max. vol.);

According to one preferred embodiment of this invention, the aforementioned spectral data therefore make it possible to simultaneously define the respective ranges of the component proportions necessary for the preparation of a target product, and to identify from among these respective ranges of the component proportions the sub-ranges allowing the preparation of the target product the value of which is at least one of the Px properties (which is preferably measured and/or calculated using the same spectral data) that satisfies the constraint of the certification process.

The fact that the spectral data makes it possible to prepare and certify the target product has advantageously opened numerous possibilities of additional applications according to this invention.

According to one preferred embodiment of this invention, at least two Px properties, for example at least three, four, five, six, seven, eight, nine, ten properties (for example advantageously selected from the aforementioned properties) were used to satisfy the constraint of the certification process of the target product; said properties having been measured and/or calculated using the spectral data used to define the respective ranges of component proportions necessary for the preparation of a target product.

Thus, in one particular embodiment of this invention, when one wishes to focus [e.g., minimize, maximize and/or average] one (or more) "Px" property(ies), the certification and preparation process will include an additional step which will consist of selecting from among said respective ranges of component proportions being fed into the mixer, the range of proportions which correspond to the preferred value of the "Px" property. The selection of a preferred value of the "Px" property [which may be minimized, maximized and/or averaged] may be dictated for various reasons, including economic reasons and/or seasonal reasons (summer/winter) and/or reasons related to changes in petroleum products and/or reasons for improved logistics management related to procurement.

Although this invention may advantageously substitute the majority of conventional methods currently used for the certification and preparation of a target product, it may happen that certain Pz properties required for the certification of the target product cannot be determined using the spectral data of this invention; thus, this invention may advantageously be combined with one or more additional steps consisting of using one or more conventional methods of measuring and/or verifying the Pz property(ies) so as to select, from among said respective ranges of component proportions being fed into the mixer, the range of proportions to which a target product corresponds in which the Pz property(ies) satisfies the constraint dictated by the certification of said target product. As an illustrative example of the Pz property, we will cite sulfur content which can be measured—preferably in line—by any suitable conventional method, for example by determination by dispersive X-ray fluorescence spectrometry at the length of the sulfur content in petroleum products.

"X" Constraint

In one particular embodiment of this invention, when we wish to focus on the use of the "X" component from among the "n" components of the target product mixture, the method of certification and preparation will include an additional step consisting of selecting from said respective ranges of the proportions of the components being fed into the mixer, the range of proportion having the highest concentration would be that of the "X" component. The constraint of use of the "X" component may be preferred (or not) for various reasons, among which are those mentioned for illustrative purposes as economic and/or periodic cleaning reasons for the "X" component storage container and/or reasons for improved logistical management linked to procurement.

Thus, in a particular embodiment, this invention also relates to the use of the aforementioned processes/methods for the preparation of a target product comprising an "X" component, the use of which consists of focusing on the use of said "X" component selected from among the "n" components of the target product mixture, the method of preparation includes an additional step of selecting from the ranges of respective proportions of the components fed to the mixer, the range of proportion having the highest concentration would be that of the "X" component.

Replacement "X'"

In another particular embodiment, this invention also consists in an improved selection method for choosing the supply of component "X'" to replace component "X", characterized in that this method comprises the following steps
 a. a spectral analysis step of component "X'" to determine a characterizing spectral datum thereof, for example a spectrum and/or a characterizing spectral database.
 b. a second step consisting of a step to replace the spectral datum characterizing component "X" with the spectral datum characterizing component "X'" in Process M.
 c. steps corresponding to Steps 1 and 3 of Process M.
 d. step 3 of Process M of the preceding steps making it possible to predict the rate of potential use of component "X'" in the target product.

This method of improved selection of the choice of procuring component "X'" to replace component "X" is particularly revolutionary in that it is no longer based solely on economic considerations. Indeed, the spectral analysis of the new component "X'" will enable the skilled person in the art to consider a multitude of factors among which we cite as examples, environmental factors, supply problems, etc.

Illustratively, the above mentioned second step may consist of either a spectral replacement step of component "X" with the spectrum of the component "X'" in the Process M1, or a replacement step from the spectral database of component "X" with the spectral database of component "X'" in Process M2.

Thus, in one particular embodiment, this invention also relates to the use of the aforementioned processes/methods for the preparation of a target product
 a. to validate the replacement of component "X" by component "X'",
 and/or
 b. predicting the potential use rate of component "X'" during preparation of a target product initially comprising component "X", the preparation process including
 a. a step to perform the spectral analysis of component "X'" to determine a characterizing spectral datum, for example a spectrum and/or a characterizing spectral database,
 b. a step consisting of a step to replace the spectral datum characterizing component "X" with the spectral datum characterizing component "X'" in the Process,
 c. a step to validate the replacement of component "X" with component "X'" and/or to predict the rate of potential use of component "X'" which makes it possible to verify that there is at least one range of respective proportions of the new components necessary for reconstitution of a spectral datum of the mixture belonging to the spectral domain of the target product.

According to one preferred embodiment of this invention, the spectral analysis method used is therefore chosen from, for example, NMR, Raman. IR, NIR and/or UV/Visible, preferably by topological spectral analysis in the near infrared ("NIR").

According to one preferred embodiment of this invention, the target product is a fuel. Among the components of fuels, we may cite by way of illustration, diesels, oxygenated gas oils, gasolines, oxygenates (for example, BOB for "blend stock for oxygenate bending"), fatty acid esters (for example FAME) esters of vegetable oil (e.g., ethyl esters and/or methyl esters), methyl tert-butyl ether (MTBE), tert-Amyl methyl ether (TAME), ethyl-Tert-butyl ether (ETBE), hydrogenated or partially hydrogenated vegetable oils ("HVO"), ethanol, bioethanols, methanol, etc. These fuels may also contain any kind of optional additives, including pro-cetane and/or pro-octane and/or pro-heptane, friction modifiers, detergents, antioxidants, cold-strength improvers, combustion improvers, anti-corrosive agents and/or mixtures thereof.

Thus, according to one embodiment of this invention, the mixture of components of target products can be made in any suitable place; by way of example, we may mention any industrial complex comprising component mixing operations for the preparation of a target product, for example a refinery, a complex (petrochemical, petroleum depot and/or any device using a product made up of a mixture of components prepared by batch and/or in-line. This invention applies more particularly to terminals or any post-refinery mixing installation, preferably a mixture of fuels.

Topological spectral analysis in the near-infrared ("NIR") field has proved particularly effective in enabling the certification and characterization of a target petroleum product and its components in accordance with this invention.

According to one embodiment of this invention, in Step 3 a computer program is used which makes it possible to calculate the ranges of respective proportions of said components necessary for reconstituting a spectral datum (spectral datum and/or spectrum and/or spectra database) of the mixture belonging to the spectral range of Step 1 from the spectral datum (data) (spectral datum and/or spectrum and/or spectra database) of Step 2. Those skilled in the art have numerous computer programs which make it possible to carry out these calculations. By way of a purely illustrative and non-limiting example, we will cite hereinafter the computer programs based on mathematical calculations using the Simplexe algorithm (any other algorithm for solving linear optimization problems may also be used) and/or computer programs based on mathematical calculations using the Nelder-Mead method (any other algorithm for solving non-linear optimization problems may also be used).

The characterization of a product according to this invention may consist in a determination and/or prediction of any chemical, physical or physico-chemical characteristic of said product and its components and/or the identification of a type and/or family of components.

Applicant's Patent No. EP0742900 is the reference of the field of topological spectral analysis. It describes a method for determining or predicting a Px value, of a property of an X material or of a property of a product resulting from a process derived from said material or from the yield of said process, which method comprises measuring the $D_i x$ absorption of said material at more than one wavelength in the region of 600 to 2600 nm, comparing the signals indicative of these absorptions or their mathematical functions with the signals indicating the Dim absorptions at the same wavelengths or their mathematical functions for a certain number of S standards in a database for which said P property or yield is known, and selecting from the database at least one and preferably at least 2 Sm standards having the Pm property, said Sm standard having the smallest average values of the absolute values of the difference at each wavelength i comprised between the signal for the material and the signal for the Sm standard in order to obtain the Px value and averaging said Pm properties or yields, when more than one Sm standard is chosen.

Topological spectral analysis has many advantages over conventional regressive mathematical methods. The numerical methods described for modeling of the physico-chemical properties of substances based on spectral analysis are correlative in nature and involve the regression relationships between the property(ies) studied. Among these multivariate analyzes are multilinear regression (MLR), main component regression (PLR), canonical regression, and partial least squares regression (PLS regression). In all cases, a relationship is sought between the property and the spectrum which may be linear but which is usually quadratic or in an upper algebraic form with regression coefficients applied to each absorption. However, the establishment of any regression requires a gradual calibration, since the approach is empirical and not supported by a theory.

These techniques have disadvantages, the main one being the need to establish a strong correlation between spectrum and property and their difficulty in dealing with the positive or negative synergy between the components contributing to this property. For example, to determine the chemical composition, for example by LINA (linear, isoparaffinic, naphthenic, aromatic) in a hydrocarbon load fed into a catalytic reformer, the use of the PLS technique based on NIR spectra was described. The model works well on the calibration set but the response of the models when adding pure hydrocarbons, e.g., cyclohexane, is not satisfactory since the model predicts variations in the isoparaffin and reverse naphthene content of those found experimentally. In addition, there are other practical difficulties, mainly due to the need to identify samples from families with the same type of relationship between the spectra and the properties to be modeled. Thus, the model may be limited, especially with a nonlinear relationship between spectrum and property. Especially when there are limitations in the data available, the accuracy of the model is reduced. The stability of the model is also a problem, as well as the necessity to carry out laborious revisions when adding new standards to obtain the new model, especially when adjusting to a new load to supply a process; thus the control of 6 properties on 4 products coming out of a distillation unit requires 24 models, each of which must be modified for each change in the feedstock not included in the calibration. Another major disadvantage encountered by these techniques arises when a point to be analyzed lies outside the previously established model; it is necessary to generate a new database and a new model per property, which makes this type of technique not only not very reactive but also requires too many hours of work.

It should be noted that the topological spectral analysis as such has not actually evolved since the Applicant's patent number EP0742900. However, this invention also provides numerous improvements to said topological spectral analysis method. The characteristics of this topological spectral analysis method, as well as its improvements and advantages, will be described in detail in the description which follows, as well as in the examples, figures and Claims. Other purposes and advantages of this invention will appear in the description, given hereafter in reference to the embodiments which are given as non-restrictive indicative examples.

Understanding of this description will be facilitated by reference to the attached FIGS. 1 to 10 and wherein:

FIG. 2 shows an example of spectral database A,

Figure 4:
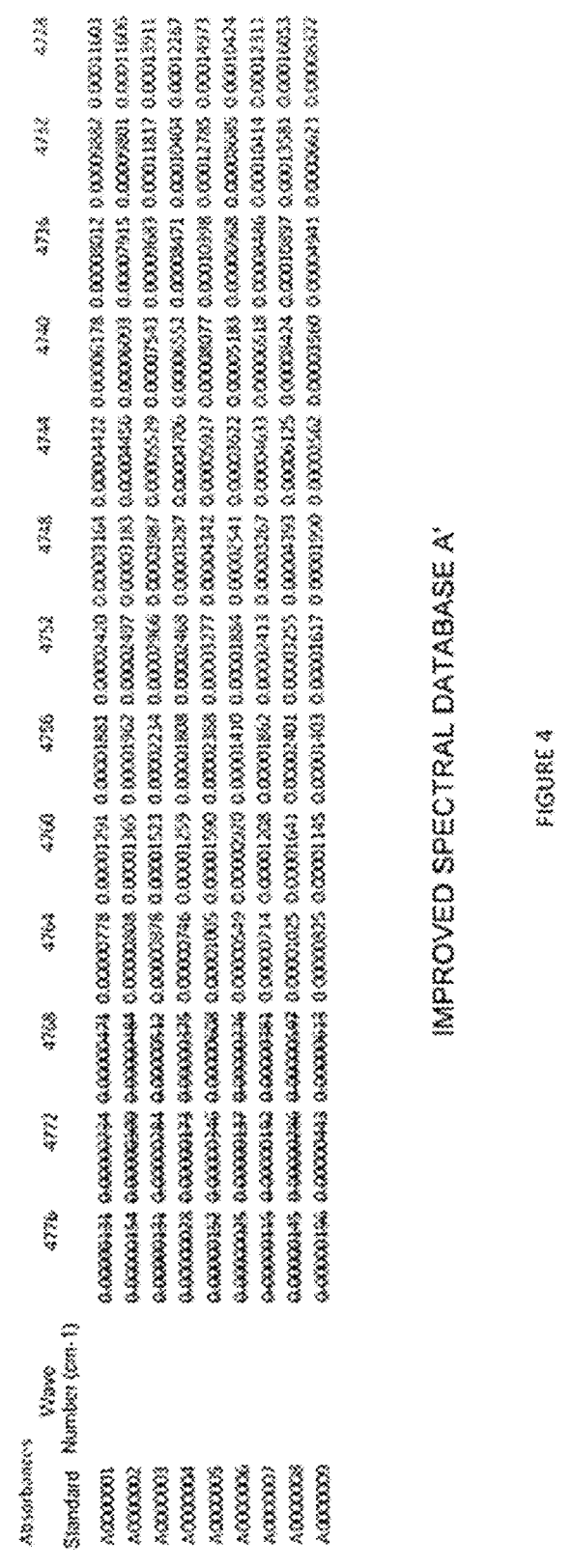
Figure 8:
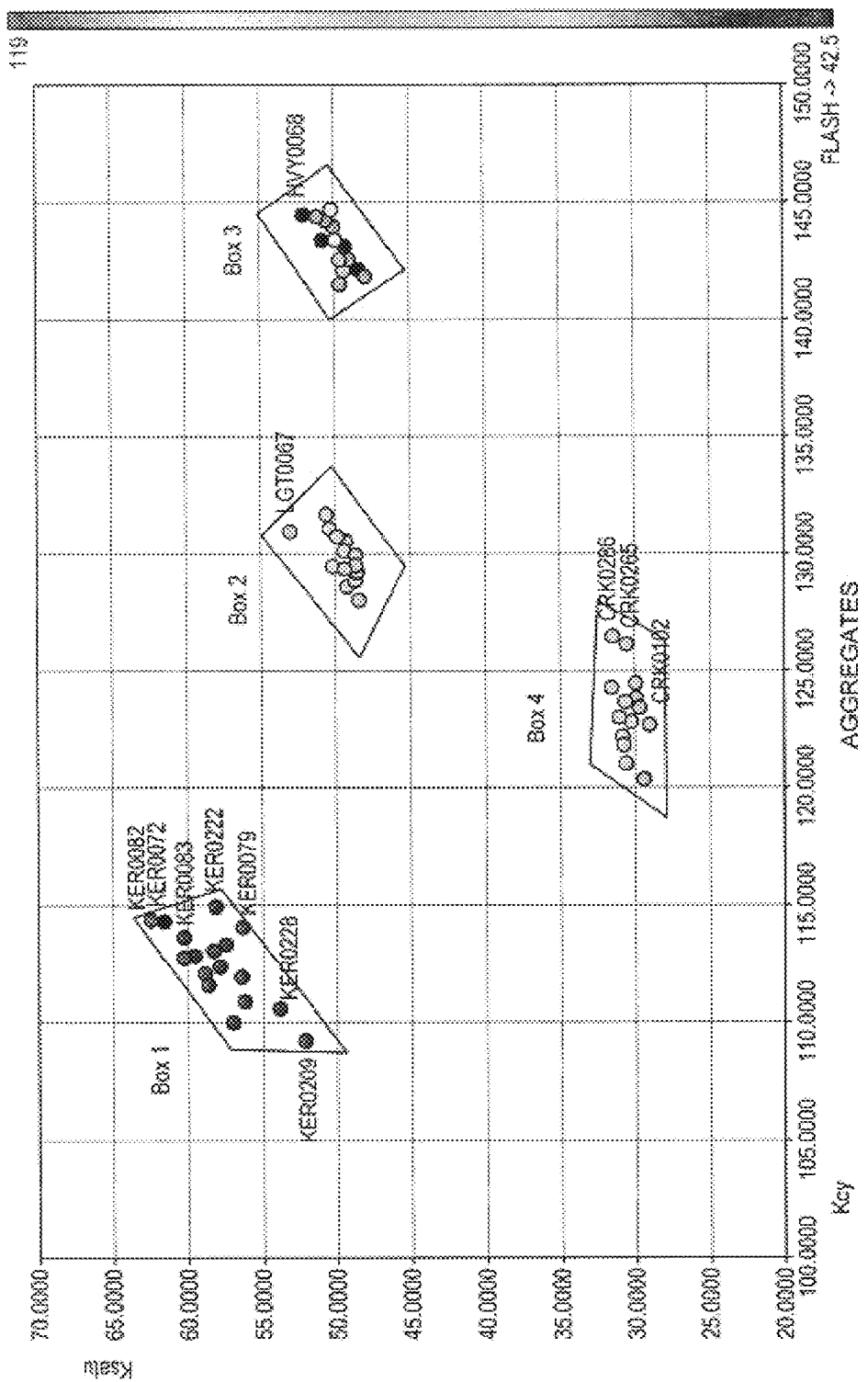

FIG. 3 shows an example of spectral database B (polluting wavelengths highlighted), FIG. 4 shows an example of an improved spectral database A' (spectral database A in which the spectral data corresponding to the polluting wavelengths have been removed), FIG. 5 shows an example of an enlarged spectral database E (spectral database A or A' in which intergerms have been added), FIG. 6 shows an example of an enlarged spectral database EE (spectral database A and/or E in which extragerms have been added), FIG. 7 shows an example of an enlarged spectral database EEI (spectral database E and/or EE in which extragerms' have been added), FIGS. 8 and 9 respectively show a graph and a table representing the discriminating aggregates, and FIG. 10 represents a spectral database of the type of that of FIG. 5 in which the measured characterizations of the standards and calculations of the intergerms have been added.

In particular, all chemometric approaches for spectral analyses from the Prior Art require the establishment of a spectral database formed from a very large initial number of samples and/or standards. Although the Prior Art cites the establishment of a spectral database based on at least 60 or at least 100 samples and/or standards, all the examples describe bases consisting of a significantly higher number of samples. This number is even greater in the chemometric approaches using regressive mathematical methods whose databases are made up of hundreds or even thousands of samples and/or standards. This invention, in one particular embodiment, makes it possible to overcome this previous requirement, which opens up a considerable number of new applications as demonstrated hereinafter.

Thus, in one particular embodiment, in a first step, the method according to this invention consists of the preparation of a database of spectra and/or spectral data of the target products and of their components, preferably a spectral and/or a broad spectrum database E for a limited number of available standard materials (and therefore representing the target products and/or their components).

This invention therefore applies more particularly to Near Infrared Spectroscopy (NIR). Indeed, NIR spectroscopy has many advantages over other analytical methods, for example in refineries, petrochemical or chemical sites as well as in all fields where the characterization of chemicals, for example hydrocarbons, in particular, fuels, and can cover a large number of repetitive applications with accuracy, speed and in-line. Moreover, the NIR region between 800 and 2500 nm contains all the molecular information in the form of combinations and harmonics of polyatomic vibrations.

In a first step, a selected type of spectral analysis is carried out on each of the standards (representative of the target product and/or its components) and we proceed to populate the spectra and/or spectral database A by recording the spectra (for example in digitized form), preferably NIR spectra, at several wavelengths (or wave numbers), for example for a limited number of available standard materials.

Figure 1:
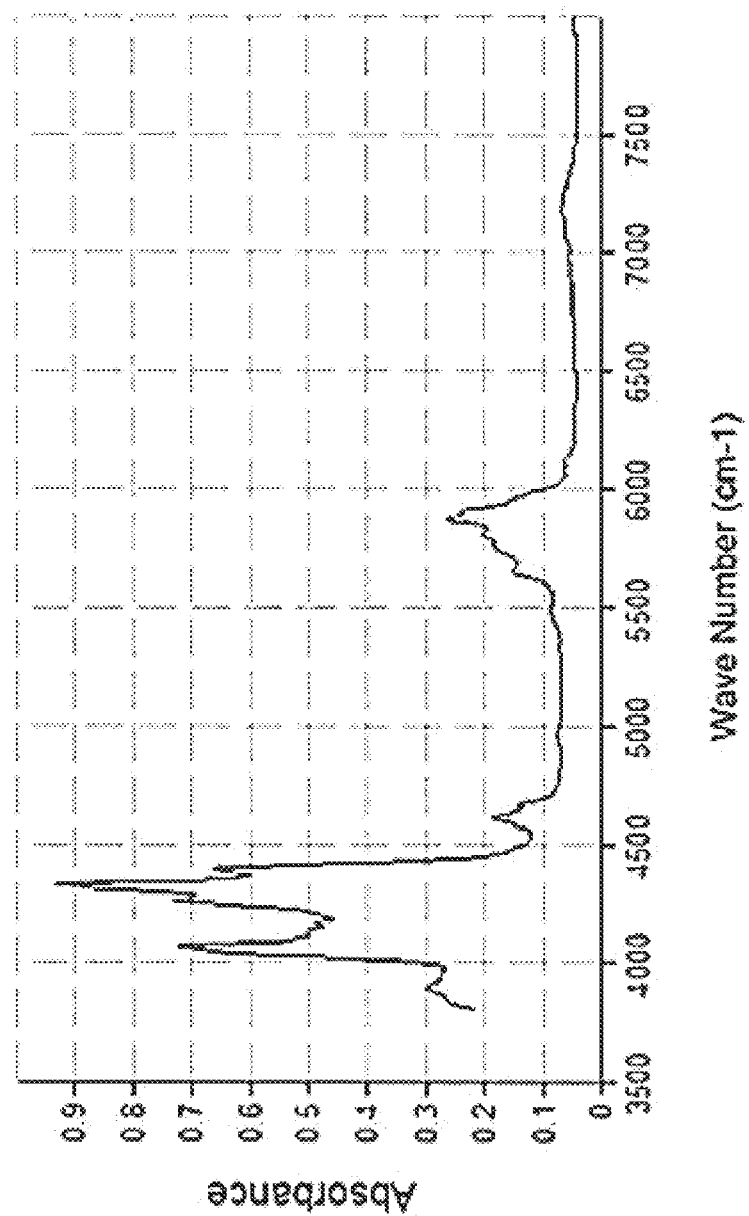
FIG. 1 shows the NIR spectrum of a standard.
Figure 2:
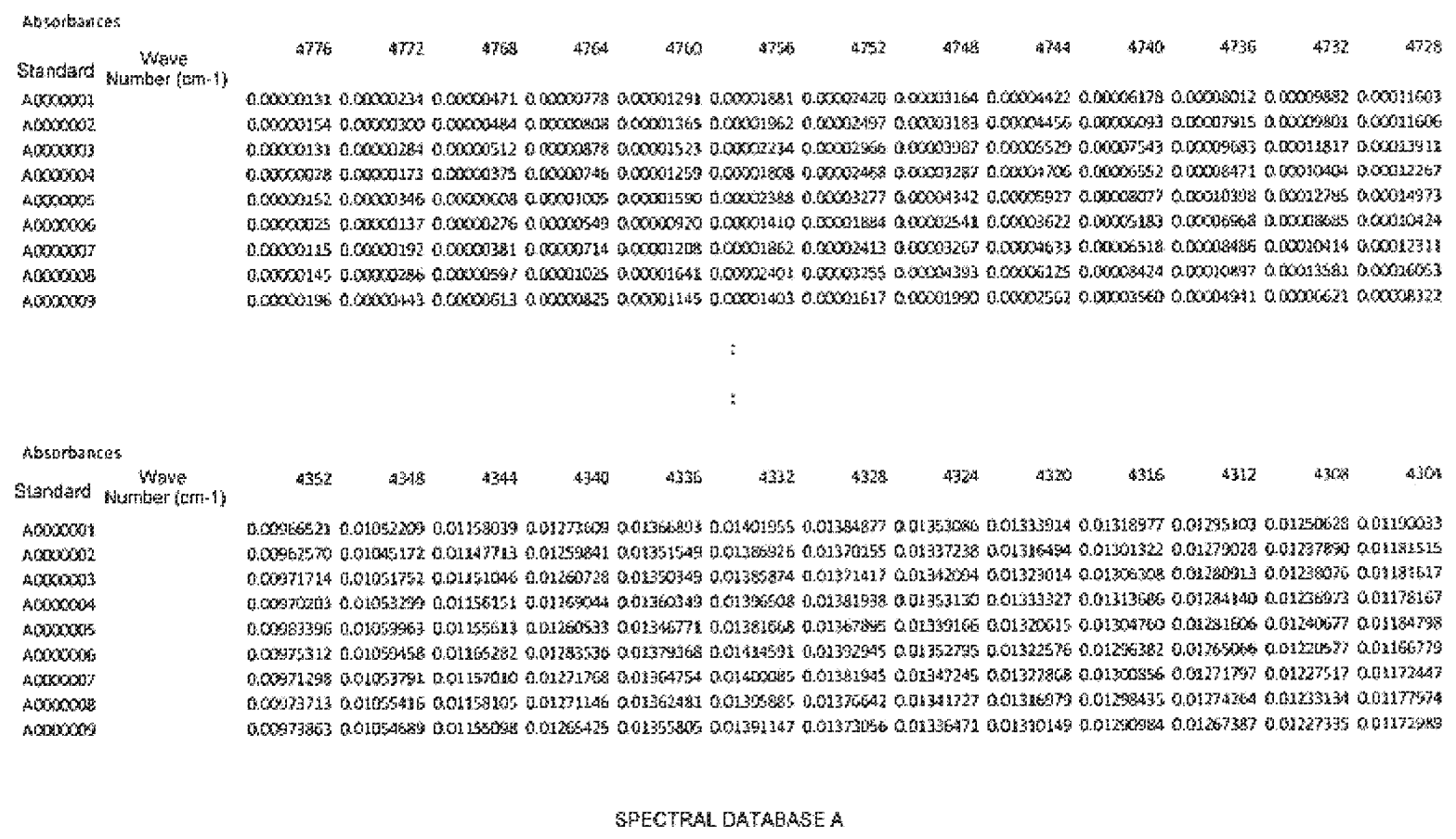

An example of the constitution and representation of this initial spectral database is described by means of FIGS. 1 and 2.

FIG. 1 shows the NIR spectrum of a standard upon which the absorbance measured as a function of the wave number may be visualized with spectral magnitude. Similar spectra are thus established identically for each standard. In the present example of representation, nine standards have been analyzed. From these spectra, a table (the spectral database A) is established, an exemplary representation of which is given in FIG. 2 for a limited number of wave numbers.

Thus, in the table of FIG. 2 (which corresponds to a truncated view—two parts of the table have been shown at different selected wavelengths), in the left column the references can be seen that make it possible to identify the nine standards and in the first line the value of the wave numbers or the ranges of wave numbers; the contents of the table therefore indicate the values of the spectral magnitude (in this case, the absorbances) which correspond to the "standard reference/wave number" pair. These spectral quantities may be any type of signals characterizing the spectra, for example the absorbances, transmittances, reflectances, etc.; the optical absorbances or densities being the most commonly used signals. By way of example, we may also mention as signals the derivatives of the absorbances or any other measurement resulting from another type of mathematical processing of said absorbances.

The limited number of available standards is usually dictated by the customer and/or end user who wish to use reliable reactive control methods while limiting the need for a large quantity of standards and the need for an analysis by conventional methods.

A characteristic of the method according to this invention is that it thus makes it possible to overcome the need dictated by the Prior Art to have a very large number of standards. For example, this invention makes it possible to characterize a sample product from less than 100 available standards, or even less than 60 or even less than 50. Very probative results have even been obtained by means of this invention from less than 40 available standards, even less than 30 or even less than 20. A minimum of 10 available standards is however preferred even if this invention has already been successfully used with a minimum of 5 available standards.

For this invention, the description thereof and the Claims hereinafter, it will be obvious to those skilled in the art that the spectra may be performed as a function of the wavelengths (and/or ranges of wavelengths) and/or as a function of the wave numbers (and/or ranges of wave numbers), because the wave number is represented by the inverse of the wavelength.

For this invention, the description thereof and the Claims hereinafter, the standards will be equally well qualified as "germs" ["G"], the two terms being interchangeable.

A second optional and preferred step according to this invention is then the elimination of "polluting" wavelengths and/or ranges of wavelengths from the spectral database A. This step consists of 1. repeating at least twice, preferably at least three times, more preferably at least five times the same spectral analysis as that performed in the first step, and this should be performed on at least one of the available standards, preferably on at least two or even on all of said standards;
2. to construct a spectral database B from the measurements made in point 1 above;
3. calculating for each selected standard from point 1 above and for each wavelength and/or range of wavelengths (from the spectral database A) the standard deviations (a) from the measurements recorded in the database B;
4. identifying the wavelengths and/or range of wavelengths in database B for which the standard deviation is greater than a predetermined value;
5. removing the measurements corresponding to the wavelengths identified in point 4 above from spectral database A.

Thus, according to one preferred embodiment of this invention, the use of the second step above makes it possible to obtain an improved spectral database A'; an example of an improved spectral database A' is shown in FIG. 4.

An example of a representation of spectral database B is shown in FIG. 3 as a table.

It can be seen that the same spectral analysis was repeated ten (10) times on the same sample and that the values for the corresponding spectral magnitudes were recorded in the table. The last three rows of the table correspond respectively and successively to the mean value of the spectral magnitude VGSmean ("VGSm") which corresponds to the sum of the values of the spectral magnitudes divided by the number ("n") of analyzes performed (VGSm=[ΣVGS]/n), with n=10 in this representation;

the standard deviation ("σ") which corresponds to the difference between VGSmax and VGSmin in each column of the table;

the ratio (σ/(VGSm/100)) whose value (in percentage) is calculated by dividing the standard deviation by the value of the mean spectral quantity, the result being multiplied by a hundred.

Thus, the last line of the table makes it possible to identify the wavelengths and/or ranges of wavelengths in database B for which the ratio ($\sigma$/(VGSm/100)) is greater than a predetermined value. According to one embodiment of this invention, within Table B one is able to identify the columns (wavelengths and/or ranges of wavelengths) for which the value of the ratios ($\sigma$/VGSm/100)) is greater than 2% (preferably greater than 1.5% or even 1%); then, said columns are deleted from database A, namely the values of the spectral magnitude corresponding to the "polluting" wavelengths. The corresponding columns (i.e., those whose wavelength and/or range of wavelengths are identical) will then be eliminated from spectral database A. It should be noted that in the above examples, Tables A and B are representations which do not have any actual relationships between them; It should also be noted that Tables A and B have been truncated to give a visual representation; in reality, said tables comprise a multitude of columns representing the wavelengths and/or ranges of wavelengths extracted from the corresponding spectrum as detailed further in the description.

An example of the representation of the improved spectral database A' is thus illustrated in FIG. 4.

An essential characteristic of the method according to this invention is that establishing the improved spectral database A' at this stage does not need to reference and/or make tire least correlation with the chemical and/or physico-chemical properties of the standards. Indeed, this second stage is totally independent.

A preferred third consecutive step of the method according to this invention is the actual enlargement of spectral database A (or the improved spectral database A'). This step consists in generating synthetic standards (also called "intergerms" ["IG"]) based on the available standards and their spectral magnitude values. For example, to generate these IGs, combinations of several available standards from the first step above can be performed and this will populate the spectral database A (or the improved spectral database A') by means of said combinations. These combinations may be performed randomly or in a directed manner as described further in the text. Said combinations may consist of any kind of mathematical process applied to the spectral magnitude values of the G standards. According to one preferred embodiment of this invention, said combination consists of a barycenter of the spectral magnitude values ("VGS") of at least two standards. It is possible, for example, to carry out these combinations between two, three or a number higher than that of the starting standards available, preferably between all available starting standards.

An example of a corresponding formula for generating a synthetic standard (IG) from the G standards (to which the VGSs correspond) is

[$\Sigma Ri \times VGSi$]/[$\Sigma Ri$]

in which i is an integer from one to the number of G standards selected for this combination and R being a real number such that

[$\Sigma Ri$]>0, and

|[$\Sigma R^*i$]|/[$\Sigma Ri$]<0.3, preferably <0.15,

And with R* representing only real negative numbers. The latter formula can also be expressed as the absolute value of the sum of the real negative numbers divided by the sum of all the real numbers.

According to one preferred embodiment of this invention, at least one of the Ri is a real negative number (R*).

By doing so, spectral database A (or the improved spectral database A) can be enlarged by means of synthetic standards (also called "intergerms" or "IGs"), thus obtaining an enlarged spectral database E.

According to one preferred embodiment of this invention, when the number of standards of spectral database A (or A') is equal to "N", the number of intergerms IG is at least greater than 1.5 N, Preferably greater than 2 N, more preferably greater than 5 N, or even greater than 10 N.

An example of a representation of the enlarged spectral database E is shown in FIG. 5 as a table. It can be seen that synthetic standards (or intergerms "IG") have been generated by mathematical combinations and that the values corresponding to spectral magnitude have been recorded in Table E. For example, we may see in Table E (FIG. 5):

six intergerms "IG" (I2G022, I2G011, I2G036, I3G038, I3G025 and I3G019;

in columns 3 to 5, the germs used to generate each of said intergerms;

in column 2, the weighting applied to the germs selected for the calculation of the VGS of the intergerms (for example, for the calculation of intergerm I2G036), a weighting of (0.44 times the germ A0000008+0.56 times the germ A0000004)) is applied.

An essential characteristic of the method according to this invention is that establishing the enlarged spectral database E at this stage does not need to reference and/or make the least correlation with the chemical and/or physico-chemical properties of the standards. In fact, this expansion step is totally independent.

A fourth additional, optional, and preferred step according to this invention then consists in further expansion of the spectral database A or the enlarged spectral database E by means of another type of synthetic standards which we will call "extragerms" ("EG"). This step is particularly pertinent when the target product to be analyzed contains a plurality of chemical compounds.

It consists, in a first sequence, of recording the spectral data of at least one spectrum corresponding to one (or more) of the chemical compounds of the target product (also called "Pole(s)"). Then, in a second sequence, the spectral database is further enlarged by using said pole(s) and by combining them with the germs "G" (a combination is performed of values of their spectral magnitude VGS).

This second sequence consists of generating synthetic standards (also called "extragerms" [EGs]) from the available Pole(s) and standards and the values of their spectral magnitude. For example, in order to generate these EGs, it is possible to combine the Pole(s) and several available standards from the first step above and populate the spectral database A and/or E by means of said combinations. These combinations may be performed randomly or in a directed manner as described further in the text. Said combinations may consist of any kind of mathematical process applied to the values of the spectral magnitudes of the G standards and of the Pole(s). According to one preferred embodiment of this invention, said combination consists of a barycenter of the spectral magnitude values ("VGS") of the selected G standards and of the Pole(s). It is possible, for example, to carry out these combinations between at least one Pole and one, two, three or a higher number of starting standards, preferably with all the available starting standards. These combinations will preferably be carried out with all the available Poles, preferably with all the Poles corresponding to all the chemical compounds constituting the target product.

An example of a formula corresponding to the generation of an EG-type synthetic standard from Pole(s) and G standards (to which the VGS corresponds) is $$[\Sigma Ri \times VGSi + \Sigma Rj \times VGSj]/[\Sigma Ri + \Sigma Rj]$$

in which i is an integer from one to the number of G standards selected for this combination, j being an integer from one to the number of pole (s) chosen for this combination
and R is an integer such that $$[\Sigma Ri + \Sigma Rj] > 0, \text{ and}$$

$$|[\Sigma R^*i]|/[\Sigma Ri + \Sigma Rj] < 0.3, \text{ preferably } < 0.15, \quad (1)$$

with R* representing only real negative numbers.
and preferably, each Rj must be such that the ratio Rj/[ΣRi+ΣRj] always falls between the opposite of the minimum content and the maximum content percentage by weight of the Poles j in the target product.

The formula (I) above can also be expressed as the absolute value of the sum of the real negative numbers "i" divided by the sum of all the integers. According to one preferred embodiment of this invention, at least one of the Ri is a real negative number (R*).

By doing so, this makes it possible to enlarge the spectral database A and/or E by means of synthetic standards "EG" ("Extragerms") and in this way, obtain an enlarged spectral database EE. Optionally, said Poles and their VGS may also be entered into the spectral database EE but this does not constitute a preferred embodiment according to this invention.

According to one preferred embodiment of this invention, when the number of standards of the spectral database A (or A') is equal to "N" and the number of "Poles" is equal to "M", the number of Extragerms "EG" is at least greater than N×M, preferably greater than 1.5 N×M, preferably greater than 2 N×M.

According to one preferred embodiment of this invention, the number of Poles is lower than 15, for example lower than 10.

According to one preferred embodiment of this invention, the number of Poles is lower than 0.2 times the number of standards, for example lower than 0.1 times the number of standards.

An example of a representation of the expanded spectral database EE is shown in FIG. 6 as the Table EE. It can be seen that the "Poles" as well as the generation of synthetic standards "EG" (extragerms) by mathematical combinations and the corresponding spectral magnitudes have been recorded in the table. For example, we may see in Table EE (FIG. 6):
  six extragerms "EG" (MEG001 to MEG006);
  in column 2 ("Pole"), the reference of the Poles used (for example, PAL054 is a particular type of alkylate used in the composition of gasolines constituting the standards of the database);
  in column 3, the reference of the germ used to generate each of said extragerms;
  in column 4, the weighting applied to the Poles (X)—the weighting applied to germs is therefore (1−X).

For example, for calculation of the extragerm MEG001, a weighting of (0.15 times the Pole PAL054+0.85 times the germ A0000009) was applied.

An essential characteristic of the method according to this invention is that establishing the expanded spectral database EE at this stage does not need to reference and/or make the least correlation with the chemical and/or physico-chemical properties of the standards. In fact this expansion step is totally independent.

A fifth additional, optional, and preferred step according to tins invention also consists of a further enlargement of the expanded spectral database E and/or EE by means of another type of synthetic standards which we shall call "extragerms'" ("EG'") Again, this step is particularly pertinent when the target product to be analyzed contains a plurality of chemical compounds.

It consists, in a first sequence, of recording the spectral data of at least one spectrum corresponding to one (or more) of the chemical compounds of the target product (also called "Pole(s)").

Then, in a second sequence, an additional enlargement of the spectral database E or EE is carried out using said Pole(s) and by combining them with the intergerms "IG" (combination of their VGS).

This second sequence consists in generating synthetic standards (also called "extragerms" ["EG"]) from the Pole(s) and the "intergerm" standards "IG" (and optionally from the genus "G") and their spectral magnitude values. For example, in order to generate these EG', combinations of the Pole(s) and several intergerms "IG" of the third step above (and optionally of "G" germs from the first step) may be performed and the spectral database E and/or EE may be populated by means of said combinations.

These combinations may be performed randomly or in a directed manner as described further in the text. Said combinations may consist in any kind of mathematical treatment applied to the values of spectral quantities of the synthetic (intergerms) "IG" standards and of the Pole(s) (and optionally of the "G" germs).

According to one preferred embodiment of this invention, said combination consists of a barycenter of spectral magnitude values ("VGS") of the intergerms IG and of the Pole(s) (and optionally of the germs "G").

It is possible, for example, to carry out these combinations between at least one Pole and one, two, three or a greater number of the "GIs" of the third step, preferably with all the "GIs"; and optionally with at least one of the germs "G", preferably with all the germs "G". These combinations will preferably be carried out with all the available Poles, preferably with all the Poles corresponding to all the chemical compounds constituting the target product.

An example of a formula corresponding to the generation of an EG'-type synthetic standard from Pole(s) and GI synthetic standards (to which the VGS corresponds) is $$[\Sigma Ri \times VGSi + \Sigma Rj \times VGSj + \Sigma Rk \times VGSk]/[\Sigma Ri + \Sigma Rj + \Sigma Rk]$$

k being an integer from one to the number of synthetic standards GI chosen for this combination, i being an integer ranging from 0 (preferably one) to the number of G standards selected for this combination, where j is an integer ranging from one to the number of Pole(s) chosen for this combination and R being a real number such that $$[\Sigma Ri + \Sigma Rj + \Sigma Rk] > 0, \text{ and}$$

$$|[\Sigma R^*i] + [\Sigma R^*k]|/[\Sigma Ri + \Sigma Rj + \Sigma Rk] 0.3, \text{ preferably} < 0.15, \quad (II)$$

preferably with Rk being always positive,
with R* representing only real negative numbers,
AND preferably, each Rj must be such that the ratio Rj/[ΣRi+ΣRj+ΣRk] always falls between the opposite of the minimum content and the maximum content percentage by weight of the Poles j in the target product.

The formula (II) above can also be expressed as the absolute value of the sum of the real negative numbers "i" divided by the sum of all the integers. According to one preferred embodiment of this invention, at least one of the Ri is a real negative number (R*).

By doing so, this makes it possible to enlarge the spectral database E and/or EE by means of synthetic standards "EG'" ("Extragerms") and in this way, obtain an enlarged spectral database EEI. Optionally, said Poles and their VGS may also be entered into the spectral database E but this does not constitute a preferred embodiment according to this invention.

According to one preferred embodiment of this invention, when the number of synthetic standards GI of the spectral database E is equal to "Z" and the number of "Poles" is equal to "M", the number of Extragerms "EG" is at least greater than Z×M, preferably greater than 1.5 Z×M, preferably greater than 2 Z×M.

According to one preferred embodiment of this invention, when the number of synthetic standards of the GI of spectral database E is equal to "Z", the number of germs G is equal to N and the number of "Poles" is equal to "M", the number of Extragerms' "E.G.,'" is at least greater than Z×M×N, preferably greater than 1.5 Z×M×N, preferably greater than 2 Z×M×N.

According to one preferred embodiment of this invention, the number of Poles is lower than 15, for example lower than 10.

According to one preferred embodiment of this invention, the number of Poles is lower than 0.2 times the number of standards, for example lower than 0.1 times the number of standards.

An example of a representation of the expanded spectral database EEI is shown in FIG. 7 as a table. It can be seen that the "Poles" as well as the generation of synthetic standards "EG'" (extragerms') by mathematical combinations and the corresponding spectral magnitudes have been recorded in the table.

For example, we may see in Table EEI (FIG. 7):
- six extragerms' "EG'" (MEP001 to MEP006);
- in column 5 ("Pole"), the reference of the Poles used (for example, PAL037 is a particular type of alkylate used in the composition of gasolines constituting the standards of the database);
- in columns 2 to 4, the reference of the intergerms (combinations of germs) used to generate each of said extragerms;
- in column 6, weighting applied. For example, for the calculation of the extragerm MEP004, a weighting of [0.9 times one intergerm (corresponding to 0.306 times the germ A00000061—0.0530 times the germ A0000009+ 0.647 times the germ A0000002)+0.1 times the Pole PAL037] is applied.

An essential characteristic of the method according to this invention is that establishing the expanded spectral database EEI at this stage does not need to reference and/or make the least correlation with the chemical and/or physico-chemical properties of the standards. In fact this expansion step is totally independent.

Therefore, this invention also relates to a method to generate and improve a spectral database (preferably used in steps one and 2 of the M2 Process for preparation of the aforementioned petroleum target product) which can be used in a method to characterize a target product and/or its components by topological spectral analysis from a limited number of available standards, in a first step the method consists of
performing the same spectral analysis on said standards, and
constituting from the spectra obtained a spectral database A with several wavelengths and/or ranges of wavelengths.

characterized in a second optional step, in which the wavelengths and/or ranges of wavelengths of "polluting" wavelengths in spectral database A are deleted from said spectral database A, the second step consisting of
1. repeating at least twice, preferably at least three times, more preferably at least five times the same spectral analysis as that performed in the first step, and this should be performed on at least one of the available standards, preferably on at least two or even on all of said available standards;
2. to construct a spectral database B from the measurements made in point 1 above;
3. calculating for each selected standard from point 1 above and for each wavelength and/or range of wavelengths (from the spectral database A) the standard deviations (o) from the measurements recorded in the database B;
4. identifying the wavelengths and/or range of wavelengths in database B for which the standard deviation is greater than a predetermined value; and
5. removing the measurements corresponding to the wavelengths identified in point 4 above from spectral database A', and also characterized by a third consecutive and preferred step consisting in the enlargement of spectral database A (or from the improved spectral database A).

This step consists of performing combinations of several standards from the first step and populating spectral database A (or the improved spectral database A) by means of said combinations (called synthetic standards or intergerms "IG") and obtaining thusly an enlarged spectral database E, and also characterized by a fourth consecutive and optional step consisting in enlarging spectral database E. This step consists of a first sequence to add to the enlarged spectral database E at least one spectrum corresponding to at least one (or more) of the chemical compounds of the target product (also called "Pole(s)") and a second sequence to perform mathematical combinations of the Pole(s) with at least one G standard from the first step and/or at least one IG standard from the third step and to populate spectral database E with said combinations (respectively called either synthetic standards extragerms "EG", or synthetic standards extragerms "EG'") and to obtain thusly an enlarged spectral database EE (or EEI).

After having built up the enlarged spectral database in accordance with the methodology developed above, it is possible to use any kind of conventional mathematical analysis to characterize a sample from the expanded spectral database.

According to one preferred embodiment of this invention, before this characterization, an additional intermediate step then consists of defining an effective discriminant method making it possible to demonstrate homogeneous subgroups of products that preferably obey the same types of properties-spectra bonds due to a strong analogy of molecular structure.

Discriminant methods can only be based on techniques for mathematical analysis (for example, factor analysis and/or principal component analysis). Although some of these mathematical methods may be useful, this invention preferably uses at least one empirical step to perform this type of discrimination. This empirical step should be based on visual analysis of the spectra of standards and/or the aforementioned poles; although this is not a preferred embodiment of this invention, this visual analysis could also be done on reconstituted spectra (from their calculated VGS) of intergerms and/or extragerms.

This empirical step makes it possible to highlight the small differences between the spectra in question, after verification that differences may be synonymous with the existence of homogeneous subgroups of products even if one might have originally thought that the entire population of products was homogeneous. Therefore, this technique allows discrimination to highlight the differences between the products of which the final user has no knowledge.

To recap, a key feature of the process to establish the extended spectral database according to a preferred embodiment of the invention above is that it was not necessary to reference and/or make any correlation with chemical and/or physico-chemical standards. According to one preferred embodiment of this invention, it is exactly the same for the discriminant step described herein.

Aggregates

Thus, according to one embodiment of this invention, the discrimination step consists of defining, from the spectral database (preferably, the enlarged version), the aggregates (preferably at least two aggregates), the n-dimensional spaces representing the combinations of the said aggregates (preferably planes—or two-dimensional spaces—representing pairs of aggregates), and the corresponding spectral boxes. According to one preferred embodiment of this invention, these aggregates and/or the n-dimensional spaces represent combinations of said aggregates and/or these spectral boxes define the spectral range of the target product and therefore the fact that the final mixture is in accordance with a significant set of specifications of the target product.

According to one embodiment of this invention, the discriminant method also includes at least two specific preferred characteristics:
1. in that said method involves an iteration phase during which the effectiveness of the spectral box is verified and therefore the pertinence of the selected aggregates; and
2. the fact that the aggregates are constructed from at least a visual analysis of the shape of the spectra which is then used to build equations from the aggregates based on the values of the spectral magnitude of the VGS.

Aggregates are defined as mathematical functions of the values of the spectral magnitude from the enlarged spectral database for grouping and/or discriminating and/or separating product families within the extended spectral database.

These aggregates can be represented generically by the function $$Agg = f(VGSi).$$

According to one preferred embodiment of this invention said function satisfies the equations of this type $$\frac{\sum_{k=1}^{n}\sum_{i=1}^{p} a_i W_i^\alpha W_k^\beta}{\sum_{i=1}^{q} a_i W_i^\alpha}$$

or preferably of the type in which $$\frac{\sum_{i=1}^{p} a_i W_i^\alpha}{\sum_{i=1}^{q} a_i W_i^\alpha}$$

W represents the discriminant values of the spectral magnitude VGS,
a are positive real numbers,
p and q represent the selection of the VGS to the wavelengths and/or relevant wavelength ranges for the discrimination step, and
$\alpha$ and $\beta$ are exponents between $\frac{1}{3}$ and 3.

As regards the iteration phase during which the effectiveness of the spectral box is verified and therefore the relevance of the selected aggregates, it suffices to add to the predetermined spectral database columns representing the equations of discriminating aggregates, calculating the value of said aggregates for each of the standards and/or intergerms and/or extragerms and or poles from the spectral database, to make the graphs (preferably in two-dimensional spaces for each pair of aggregates), and to thus see whether discrimination has led to the identification of homogeneous product subgroups. This discrimination step makes it possible to divide the spectral database into several (at least two) different families (homogeneous product subgroups), preferably with at least three different families.

By way of example, FIGS. 8 and 9 respectively show
a graph whose abscissa/ordinate axes correspond to two discriminating aggregates, and
a table of corresponding values whose columns represent several discriminating aggregates, the first two of which were used in the creation of the graph (FIG. 8).

These Figures clearly show how we manage to highlight several homogeneous product subgroups; which makes it possible to select the spectral range of the target product.

Therefore, this invention also relates to a method for characterizing a product by topological spectral analysis.

The characterization of a product according to this invention may consist of determining and/or predicting any chemical, physical or physico-chemical characteristic of said product.

According to one preferred embodiment of this invention, the first step was therefore characterized by establishing a spectral database, preferably an enlarged spectral database as described in this description.

As already indicated above, the graphic representations of the databases (tables) in the accompanying Figures are truncated views because in reality said databases include a plurality of columns representing the wavelengths and/or ranges of wavelengths (or as an equivalent, the wave numbers or range of wave numbers) extracted from the corresponding spectra.

According to one preferred embodiment of this invention, the number of wavelengths selected may be from two to 1000, for example from five to 200 or from 40 to 80.

The wavelengths chosen may be at regular intervals such as one to 50 nm or every 10 to 50 nm or every 15 to 35 nm or everyone to 5 nm or every nanometer, or they may be at irregular intervals, for example, at intervals of one to 200 nm, for example from one to 100 or from one to 50, in particular, from two to 50 or from four to 50 or from 10 to 60 nm, which may be selected or random due to a variation in the shape of the spectral curve at that wavelength e.g., a peak, a valley or shoulder or chosen with chemical or statistical criteria, such as factor analysis. The wavelengths may be in the region 600 to 20000 nm, for example from 625 to 2600 nm, for example from 800 to 2600 nm, in particular from 1500 to 2600 or from 2000 to 2550 nm. The wave numbers can be in the region of 16600 to 500, for example from 16000 to 3840 cm-1, for example from 12500 to 3840 cm-1, in particular from 6660 to 3840 or from 5000 to 3900 cm-1; the corresponding frequencies in Hertz can be obtained by multiplying these wavelengths by 3×10 (exp) 10 cm/s.

Before you can identify and/or predict the property of a sample, it is obviously necessary to measure the values of the said property to the standards and, optionally, to the poles. Thus, in one embodiment of this invention, the chemical, physical and/or physico-chemical standards (and optionally the poles) are determined using conventional analytical techniques. By way of a non-limiting example of the conventional analytical techniques, we may mention gas chromatography for chemical compositions. Although it goes without saying that the standards are selected to cover the range in which the method is to be used, in a preferred embodiment, this invention provides for working with a limited number of standards through the methodology of enlarging the aforementioned spectral database.

Thus, in one preferred embodiment of this invention, the values of the desired properties measured for said standards (and optionally for the poles) are added to the spectral database; when the spectral database is enlarged, the values of said properties for synthetic standards intergerms (and optionally for the extragerms) are then calculated from the formulas used to generate the synthetic standards; this calculation is done simply by replacing the spectral magnitude values VGS with the measured values of said properties of the standards (and optionally the poles) used in the formulas (and optionally, for the extragerms, by the values already calculated for the intergerms). This leads to a spectral database consisting of a number of points (standards and optionally the intergerms, the poles and the extragerms) which are associated with the desired properties (measured and calculated). An example of an embodiment (truncated view) is given in FIG. 10.

This is illustrative of an enlarged spectral database E consisting of standards (A) and intergerms (IG). The table has been supplemented by the characteristics of the desired target products, namely RON and MON values (Research Octane Number (RON) and Motor Octane Number (MON)). These characteristics were therefore measured for the standards and calculated for the intergerms.

In the description of EP0742900, the signals are compared, e.g., the absorptions (or their derivatives) for the unknown sample, with the signals. e.g., absorptions (or their derivatives) at the same wavelength of the standards, and the standards having the smallest differences are chosen. Then the properties of these standards chosen are averaged to determine the property of the unknown sample.

Therefore, a calculated spectrum is reconstituted from the target product to which the characteristic (property) is thus calculated.

According to a preferred embodiment of this invention, this comparison of signals is therefore not performed on the entire spectral database, but only the portion of the spectral database representative of the homogeneous subgroup to which the sample belongs. This is done preferably by using the above-mentioned discriminant method (discriminant aggregates) that is defined in this part of the spectral database.

Then, the signals are compared. e.g., the absorptions (or their derivatives or any other value of spectral magnitude) for the unknown sample (target product), with the same signals and at the same wavelength of the standards and/or intergerms and/or extragerms and/or poles belonging to the same homogeneous subgroup, and the standards and/or intergerms and/or extragerms and/or the poles having the smallest differences is chosen in the spectral database.

Whatever the method is used, the points nearest to the target product will later be called "close neighbor". Then, for example, averaging such properties can make these standards and/or intergerms and/or extragerms and/or poles selected may be used to determine the desired characteristic (property) of the unknown sample.

In accordance with one particular embodiment of this invention, the close neighbor chosen are those with the smallest average values of the absolute difference at each wavelength i between the value of spectral magnitude (represented for example by the absorbance or a derivative thereof) Wix for the target product (sample/unknown product) and the signal corresponding to Wim for the close neighbor. The averages may relate for example to the average value of Wix−Wim (regardless of its sign, i.e., an absolute difference), or of (Wix−Wim) exp2. Each close neighbor in the spectral database for the type of product in question, we find the average difference as described and we choose the closest neighbor having the smallest average differences, namely at least one but preferably two, up to 1000 of the smallest, for example two to 100 or two to 20, but especially from two to 10 and especially two to 6 of the smallest. This selection of closest neighbors can be performed by any known method, for example, the methods described in the description of patent No. EP0742900 can be used advantageously (for example to determine the proximity index).

According to one particular embodiment of this invention, the number of close neighbor may be equal to one, preferably greater than or equal to two, even preferably greater than or equal to three.

According to one embodiment of this invention, the number of close neighbor is less than or equal to 50, for example less than or equal to 20, or even 10.

As stated previously, from the time the "close neighbor" points were selected, one can easily average the selected properties of these close neighbor (standard and/or intergerms and/or extragerms and/or poles) to determine the property of the unknown sample (the target product). Therefore, a calculated spectrum is reconstituted from the target product to which the characteristic (property) is thus calculated.

However, and this is a preferred embodiment of this invention, the applicant has unexpectedly found a significant improvement in the accuracy and robustness of its method for determining the desired characteristic (e.g., a property) of a target product when performing a weighted average of the properties of these "close neighbor" points (which may be standards and/or intergerms and/or extragerms and/or poles), said weighting being an inversely proportional linear or non-linear function to the distance between the sample ("the target product") and the "close neighbor" points selected; this weighting may for example be represented by the formula $$\text{POND} = \frac{\frac{1}{di^a}}{\sum_{1}^{n} \frac{1}{di^a}}$$

With a being a positive number, preferably between 0.5 and 1.5, di is the distance between the target product and the close neighbor i, and n is the total number of close neighbor.

Therefore, a weighting of this kind in the measured properties (and optionally calculated) of "close neighbor" is applied to obtain the property of the target product.

Therefore, a calculated spectrum is reconstituted from the target product to which the characteristic (property) is thus calculated.

In other words, the calculation of characteristic Z of the target product is achieved through the corresponding characteristics Zi of the close neighbor points, while allowing characteristics of said close neighbor points a much greater weight in said calculation in that they are closer to the target product.

Thus, this invention also provides a method of characterizing a target product comprising the following steps:
1. Establishment of a spectral database comprising samples, their spectra and their measured characteristics ("CAR", for example the property "P"),
2. Spectral analysis of the target product and comparison of the obtained spectrum (Spectrum PC) with the spectral data from the database.
3. Identification of the "close neighbor" points of the target product, and
4. Calculate by topology the characteristic of the target product (CARpc/top, for example the property Ppc/top) according to the corresponding characteristic close neighbor points, characterized in that the calculation of step 4 is based on a weighting related to the inverse of the distance between the target product and the close neighbor points.

One can use the method of the invention to determine more than one property P at a time. For example at least two, in particular from one to 30 for example two to 10 properties at a time. Of course we can use different numbers of standards chosen for each property.

In another preferred embodiment of this invention, the Applicant has discovered a particularly effective alternative method.

This method involves combining one of the topological characterization methods of the aforementioned target product with any mathematical model that differs from the topological methods (preferably a regression model) and that makes it possible to characterize the target product from the spectral magnitude values VGS (for the same property).

This method thus requires prior establishment of a mathematical model that can calculate the properties of products based on spectral magnitude values (VGS) from the database, preferably a regression model (product characterization from the pre-established spectral database); this spectral database can be either the aforementioned database A or preferably database A', E, EE or EEI, or a selection of said databases. Preferably, this database will be the same as that used for the topological method.

This alternative method for characterizing a target product comprises the following steps:
1. Establishment of a spectral database comprising samples, their spectra and their measured characteristics ("CAR", for example the property "P"),
2. Spectral analysis of the target product and comparison of the obtained spectrum (Spectrum PC) with the spectral data from the database.
3. Identification of the "close neighbor" points of the target product,
4. Calculation by topology
    4.1. of the characteristic of the target product (CARpc/top top, e.g., property PPC/top) and
    4.2. of its thusly calculated spectrum (spectrum PCcalc),
5. Establishment from the spectral database of a mathematical model to calculate the characteristic of a product from the spectral database (CAR/mod, for example property P/mod)
6. Calculation of the characterization of the target PC product using the following formula=CARpc=CARpc/top+[CARpc/mod−CARpccalc/mod]
    with
    CARpc being the calculated value of the characteristic of the desired target product.
    CARpc/top is the value calculated by topology (close neighbor points) of the characteristic of the target product,
    CARpc/mod being the value calculated by the mathematical model of the characteristic of the target product, and
    CARpccalc/mod being the value calculated by the mathematical model of the characteristic of the calculated target product (using the spectral data obtained in point 4.2).

The characterization of a product according to this invention may consist in a determination and/or prediction of any chemical, physical or physico-chemical characteristic of said product and/or the identification of a type and/or family of products.

For example, the presence of individual chemical compounds within one compound may be determined as well as their concentrations; any type of property can also be determined, some of which are exemplified below.

Thus the method can be used for the physico-chemical determination or prediction regarding at least one feedstock or a product used in an industrial oil refining process and/or petrochemical operations or obtained in aid thereof. The process can be a hydrocarbon conversion or separation process, preferably a process of reforming or catalytic cracking or hydro-processing, or distillation or blending. In particular, the following may be used to determine at least one property of a feedstock and/or to predict and/or determine at least one property and/or the yield of a product from a certain number of different processes such as processes for separating petroleum products such as atmospheric distillation, vacuum distillation or distillative separation, under greater than atmospheric pressure, and thermal or catalytic conversion, with or without partial or total hydrogenation of a petroleum product, such as catalytic cracking, for example, fluid catalytic cracking (FCC), hydrocracking, reforming, isomerization, selective hydrogenation, visbreaking or alkylation. In particular, this invention applies to the mixture of components of the target products (e.g., target petroleum products, for example, fuels) in any suitable place, for example a refinery, an oil terminal and/or any device using a target product made of a mixture of components prepared in batches and/or preferably in-line.

The use of the method in mixing operations involving the production and/or determination of at least one property of a liquid hydrocarbon mixture (optionally with other additives, such as alkyl ethers) is of particular value. This method may comprise or may not comprise the determination of each component of the mixture of a mixture index for the property sought. In this method as applies to the mixture, one can simply obtain the blend index by calculation and without having to prepare the physical mixtures of standards other than those contained in the database. The mixing indices may be combined linearly (or nonlinearly) in the areas of stability to determine from the value of this combination, a value for at least one property of the resulting mixture.

The mixture can be created by mixing at least two compounds chosen from butane, hydrogenated steam cracked gasoline, isomerate, reformate, methyl-ter-butyl-ether (MTBE) and/or tert-Amyl methyl ether (TAME) and/or ethyl-ter-butyl-ether (ETBE), derived by FCC gasoline, ethanol and/or bioesters. This process may be repeated by digitally adding the other components separately to the liquid hydrocarbon base to determine a series of mixing indices and then determining from these indices the properties of the multi-component mixture.

Examples of properties that can be determined and/or predicted are the following: for automotive fuels/gasolines, at least one of the Research Octane Number (RON), the Motor Octane Number (MON) and/or their arithmetic mean, with or without additives and/or the content of methyl-t-butyl ether or methylisoamyl ether and/or benzene.

For automotive fuels/gasolines, at least one of the vapor pressures, density, volatility, distillation curve, such as the percentage distilled at 70° C. and/or 100° C., the oxygen content or the content of benzene or sulfur, the chemical composition and/or for example, the gum content expressed in mg/100 ml (especially to determine these properties for use in the mixing operations).

For diesel or gas oil fuels, at least one cetane number (e.g., measurement at the motor), the calculated cetane index, cloud point, the "discharge point", the filtering ability, the distillation curve, the density. e.g., 15° C. the flash point, e.g., the viscosity at 40° C., the chemical composition, the sensitivity to additives and the percentage of sulfur.

For the distillation of products produced from crude oil, e.g., at atmospheric pressure, at least one of densities, percentage of sulfur, viscosity at 100° C., the distillation curve, the paraffin content, the residual carbon content or Conradson carbon content, the content of naphtha, the flash point of the oil, the cloud point for diesel fuel, e.g., light gas oil and/or the viscosity at 100° C. and/or the content sulfur for the atmospheric residues and the yield for at least one of the cuts, gasoline (bp. 38-95° C.), benzene (bp. 95 at 149° C.), naphtha (bp. 149 to 175 C), kerosene (bp. 175 to 232° C.), light gas oil (bp. 232 to 342° C.), heavy gas oil (bp. 342 to 369° C.) and that of the upper atmospheric residue to 369° C.

For at least one of a feedstocks or products of a catalytic cracking process e.g., an FCC process, at least one of densities, percentages of sulfur, the aniline point, the diesel index, the fuel index, viscosity at 100° C., refractive index at 20° C. and/or at 60° C., the molecular weight, the distillation temperature e.g., the distillation temperature at 50, the percentage of aromatic carbon, the total nitrogen content and the factors characterizing the crackability of the feedstock e.g., Kuop, the crackability factor, the cokability factor and the yield e.g., in gas, gasoline, gas oil or residue. Thus, it is possible to determine the yields and/or properties of the various products obtained by distillation of the cracked products such as RON and/or MON without an anti-knock additive for gasoline cutting and viscosity at 100° C. for the distillation residue.

For at least one of the products or feedstock from a catalytic reforming process, at least one of the densities, the distillation temperatures and/or chemical compositions (expressed in percentages) of linear saturated hydrocarbons, isoparaffins, naphthenes, aromatics and olefins.

For at least one of a products or a feedstocks for a gasoline hydrogenation process, at least one of the densities, the distillation temperature, RON and/or MON, the gasoline vapor pressure without anti-knock additives or lead, volatility, chemical composition (expressed as a percentage) in linear saturated hydrocarbons, isoparaffins, naphthenes, aromatic substances such as benzene and mono/di-substituted benzene, olefins such as cyclic and non-cyclic olefins, diolefins, and the index of maleic anhydride.

It must be obvious to the skilled person that this invention allows embodiments in many other specific forms without departing from the scope of the invention as claimed. In this way, these embodiments must be considered to be for illustrative purposes being able to be modified within the domain defined by the scope of the attached Claims.

The invention claimed is:

1. A Method for certification and preparation of a target product for batch and/or in-line mixing of its "n" components from different flows from said components at controlled concentrations and/or flow rates, with optional incorporation of additives, said target product having to be marketed with a set of ranges of physico-chemical characteristic values, method in which a batch and/or continuous mixer is fed said components at controlled concentrations and/or flow rates, this method being characterized in that:
   1. at least one spectral datum characterizing the target product is available and which defines its spectral range, the value of said spectral datum responding to at least one condition of the certification method,
   2. spectral datum (data) is (are) available, each individually characterizing at least two components of the target product,
   3. a computer program is used which makes it possible to calculate the ranges of respective proportions of said components necessary for reconstituting a spectral datum of the mixture belonging to the spectral range of Step 1 from the spectral datum (data) of Step 2, and
   4. the ranges of respective proportions of the constituents of step 3 are used to control the concentrations and/or flow rates of the components fed into the mixer so as to prepare the target product whose value of said spectral datum satisfies the same condition (or same conditions) of the certification method of the first Step.

2. The Method according to claim 1 characterized in that the spectral data are measured using the same type of spectral analysis.

3. The Method according to claim 1 characterized in that the spectral data are spectra and/or spectral databases.

4. The Method according to claim 1 characterized in that the spectral data are obtained from spectral analysis chosen from NMR, Raman, infrared (IR), near-infrared (NIR) and/or UV/Visible.

5. The Method according to claim 1 characterized in that the number of "n" components of the target product is greater than or equal to three.

6. The Method according to claim 1 characterized in that it performs an additional step following the second step of claim 1, said additional step consisting of the constitution from the spectral data characterizing the components of new spectral data characterizing the mixtures of said components, and then using these new spectral data in the third step of claim 1.

7. The Method according to claim 1 characterized in that the target product is a petroleum product, a fuel, a gas oil and/or a gasoline.

8. The Method according to claim 1 characterized in that the preparation is carried out in a refinery, a (petro-) chemical complex, a petroleum depot and/or any plant using a batch and/or in-line mixture of components.

9. The Method according to claim 1 further comprising preparing a target product comprising:
   measuring and/or verifying the property(ies) Pz so as to select, from among said ranges of respective proportions of the components feeding the mixer, the range of proportions to which a target product whose Pz property(ies) satisfies the constraint dictated by the certification of said target product corresponds, said Pz property being the sulfur content of the petroleum product whose in-line measurement—is carried out by wavelength-dispersive x-ray fluorescence spectrometric determination of the sulfur content in the petroleum products.

10. The Method according to claim 1 further comprising preparing a target product which comprises:
   selecting from said respective ranges of component proportions being fed into the mixer, the range of proportions at which the preferred value of one or more of the "Px" properties will correspond, the said property(ies) having been measured and/or calculated using the spectral data used to define the range of properties of the respective proportions of the components required for the preparation of a target product.

11. The Method according to claim 1 further comprising preparing a target product comprising a component "X", which comprises:
   favoring the use of said component "X" from among the "n" components of the target product mixture, and
   selecting from the ranges of respective proportions of the components being fed into the mixer, the proportion range having the highest concentration of "X" component.

12. The Method according to claim 1 further comprising:
   a. validating the replacement of component "X" by component "X'", and/or
   b. predicting the potential use rate of component "X" during preparation of a target product initially comprising component "X", the preparation process including:
      a. a spectral analysis step of component "X'" to determine a characterizing spectral datum,
      b. a step of replacing to replace the spectral datum characterizing component "X" with the spectral datum characterizing component "X" in the Process,
      c. a validation step to replace an "X" component with an "X'" component and/or to predict the potential rate of use of the component "X'" for the third step of claim 1 that makes it possible to verify that at least one range exists of the respective proportions of the new components necessary to the reconstitution of a spectral datum of the mixture belonging to the spectral domain of the target product.

13. The Method according to claim 1, the spectral data individually characterizing all the "n" components of the target product.

14. The Method according to claim 2, wherein the spectral data are measured using the same type of spectrometer.

15. The Method according to claim 4, wherein the spectral data are obtained from near-infrared topological spectral analysis ("NIR").

16. The Method according to claim 8, wherein the preparation is carried out in a terminal or any post-refinery fuel mixing facility.

* * * * *